United States Patent
Carroll et al.

(10) Patent No.: US 11,998,426 B2
(45) Date of Patent: Jun. 4, 2024

(54) CUTTING TEMPLATE FOR A NEGATIVE PRESSURE WOUND THERAPY DRAPE

(71) Applicant: KCI LICENSING, INC., San Antonio, TX (US)

(72) Inventors: Christopher A. Carroll, San Antonio, TX (US); Matthew F. Cavanaugh, II, San Antonio, TX (US); Shannon C. Ingram, Bulverde, TX (US); Justin Rice, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 896 days.

(21) Appl. No.: 17/045,213

(22) PCT Filed: Apr. 5, 2019

(86) PCT No.: PCT/US2019/025967
§ 371 (c)(1),
(2) Date: Oct. 5, 2020

(87) PCT Pub. No.: WO2019/199596
PCT Pub. Date: Oct. 17, 2019

(65) Prior Publication Data
US 2021/0161721 A1 Jun. 3, 2021

Related U.S. Application Data
(60) Provisional application No. 62/656,642, filed on Apr. 12, 2018.

(51) Int. Cl.
*A61F 13/05* (2024.01)
*A61B 46/20* (2016.01)
(Continued)

(52) U.S. Cl.
CPC .............. *A61F 13/05* (2024.01); *A61B 46/20* (2016.02); *A61M 1/90* (2021.05); *A61F 13/15723* (2013.01)

(58) Field of Classification Search
CPC .. A61F 15/02; A61F 13/00068; B26F 1/3846; A61M 1/912
See application file for complete search history.

(56) References Cited

U.S. PATENT DOCUMENTS 124,669 A * 3/1872 Delkescamp .......... B26D 3/003
83/53
1,355,846 A 10/1920 Rannells
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Catharine L Anderson
*Assistant Examiner* — Arjuna P Chatrathi

(57) ABSTRACT

A cutting template for use with a negative pressure wound therapy system includes a substantially rigid body. The body includes a top surface, a bottom surface, a height, and a recess. The top surface is configured to engage a drape layer. The bottom surface is configured to engage a dressing layer. The height is defined between the top surface and the bottom surface. The height is configured to create a gap between the drape layer and the dressing layer. The recess is disposed substantially about a perimeter of the body. The recess is
(Continued)

configured to receive an edge of a cutting tool so that an opening is formed in the drape layer when the edge is traversed about the perimeter.

17 Claims, 23 Drawing Sheets

(51) Int. Cl.
  *A61M 1/00* (2006.01)
  *A61F 13/15* (2006.01)

(56) References Cited

U.S. PATENT DOCUMENTS

| | | | |
|---|---|---|---|
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| D221,684 S | 8/1971 | Martel | |
| 3,648,692 A | 3/1972 | Wheeler | |
| 3,682,180 A | 8/1972 | McFarlane | |
| 3,826,254 A | 7/1974 | Mellor | |
| D244,996 S | 7/1977 | Martin | |
| 4,080,970 A | 3/1978 | Miller | |
| 4,096,853 A | 6/1978 | Weigand | |
| D250,094 S | 10/1978 | Forsman et al. | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| D257,656 S | 12/1980 | Walker | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| D266,820 S | 11/1982 | Ferrin | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,426,781 A * | 1/1984 | Kufrin | B26F 1/3846 30/310 |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,007,320 A * | 4/1991 | Craig | B26F 1/3846 30/310 |
| 5,037,397 A | 8/1991 | Kalt et al. | |
| 5,079,843 A * | 1/1992 | Shelton | B23B 51/05 30/310 |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| D330,520 S | 10/1992 | Meadows | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,357,972 B1 * | 3/2002 | Zendler | B23B 51/05 30/310 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| D540,202 S | 4/2007 | Welch | |
| 7,651,484 B2 | 1/2010 | Heaton et al. | |
| 8,394,081 B2 | 3/2013 | Locke et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0243073 A1* | 12/2004 | Lockwood | A61F 17/00 602/41 |
| 2012/0116334 A1* | 5/2012 | Albert | A61M 1/913 604/319 |
| 2013/0035649 A1 | 2/2013 | Locke et al. | |
| 2013/0231621 A1 | 9/2013 | Aali et al. | |
| 2014/0163486 A1* | 6/2014 | Riesinger | A61M 1/915 604/319 |
| 2014/0163487 A1 | 6/2014 | Tout et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |

(56) References Cited

FOREIGN PATENT DOCUMENTS

| | | |
|---|---|---|
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2013043972 A1 * | 3/2013 .......... A61M 1/0086 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sept. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ? uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.
"ROSENICE Spulen Metall gultig fur Nahmaschine 10pcs (Silber)," retrieved from https://www.amazon.de/ROSENICE-Spulen-Metall-g%C3%BCltig-N%C3%A4hmaschine/dp/B0743BBDW6/ref=sr_1_fkmr0_1?_mk_de_DE=%C3%85M%C3%85%C5%BD%C3%95%C3%91&keywords=ROSENICE Spulen Metall gUltig fUr N~hmaschine 10pcs %28Silber%29&qid=1562858978&s=gateway&sr=8-1-fkmr0 on Jul. 11, 2019, 10 pages (with machine translation).
"Shunshida Lot de 25 bobines vides Fr metal pour Machine a coudre Singer Brother/Janome (Transparent)," retrieved from https://www.amazon.fr/Shunshida-bobines-Machine-Brother-Transparent/dp/B006GNMUDK/ref=sr_1_1?_mk_fr_FR=%C3%85M%C3%85%C5%BD%C3%95%C3%91&keywords=Shunshida Lot de 25 bobines vides Fr metal pour Machine a coudre Singer Brother%2FJanome %28Transparent%29&qid=1562859282&s=gateway&sr=8-1 on Jul. 11, 2019, 14 pages (with machine translation).
International Search Report & Written Opinion in International Application No. PCT/US2019/025967 dated Jul. 4, 2019, 17 pages.

\* cited by examiner

CUTTING TEMPLATE FOR A NEGATIVE PRESSURE WOUND THERAPY DRAPE

CROSS-REFERENCE TO RELATED APPLICATIONS

This application is a U.S. National Stage Applicaton of PCT/US2019/025967, filed Apr. 5, 2019, which claims the benefit of priority to U.S. Provisional Application No. 62/656,642, filed on Apr. 12, 2018, the entire contents of each of which are incorporated herein by reference in their entireties.

BACKGROUND

The present disclosure relates generally to wound therapy systems and devices, and more particularly to a cutting template for a negative pressure wound therapy drape.

Negative pressure wound therapy (NPWT) is a type of wound therapy that involves applying negative pressure (relative to atmospheric pressure) to a wound site to promote wound healing. Some NPWT systems surround the wound in a dressing which is sealed with a drape. The drape establishes a barrier between negative pressure and atmospheric pressure. These NPWT systems may include sensors for monitoring the negative pressure within the drape. The drape must be cut in order for these sensors to be installed. Cutting the drape may be difficult due to adherence between the drape and dressing. In some instances, the NPWT system may not operate desirably if the drape is cut incorrectly.

SUMMARY

One implementation of the present disclosure is a cutting template for use with a negative pressure wound therapy system includes a substantially rigid body. The body includes a top surface, a bottom surface, a height, and a recess. The top surface is configured to engage a drape layer. The bottom surface is configured to engage a dressing layer. The height is defined between the top surface and the bottom surface. The height is configured to create a gap between the drape layer and the dressing layer. The recess is disposed substantially about a perimeter of the body. The recess is configured to receive an edge of a cutting tool so that an opening is formed in the drape layer when the edge is traversed about the perimeter.

In some embodiments, the bottom surface includes a dimple protruding from the bottom surface.

In some embodiments, the top surface includes a plurality of graduation marks, each of the plurality of graduation marks corresponding with a circumferential location about the top surface.

In some embodiments, the cutting template further includes a hole centered on a center point of the top surface and extending from the top surface through the body to the bottom surface.

In some embodiments, the bottom surface is at least one of textured and coated with a non-slip coating.

In some embodiments, the cutting template further includes a first annular surface and a second annular surface. The first annular surface is disposed between the top surface and the bottom surface. The second annular surface is contiguous with the top surface and extends towards the bottom surface. At least part of the recess is formed between the first annular surface and the second annular surface.

In some embodiments, the cutting template further includes a first annular surface and a second annular surface. The first annular surface is disposed between the top surface and the bottom surface. The second annular surface is disposed between the top surface and the bottom surface. At least part of the recess is formed between the first annular surface and the second annular surface. The first annular surface is substantially orthogonal to the second annular surface.

In some embodiments, the cutting template further includes a first annular surface and a second annular surface. The first annular surface is contiguous with the bottom surface and extends orthogonally from the bottom surface towards the top surface. The first annular surface is defined by a first diameter. The second annular surface is contiguous with the top surface and extends orthogonally from the top surface towards the bottom surface. The second annular surface is defined by a second diameter different from the first diameter. One of the first annular surface and the second annular surface is inset relative to the other of the first annular surface and the second annular surface to form the recess.

Another implementation of the present disclosure is a cutting template for use with a negative pressure wound therapy system. The cutting template includes a top surface, a bottom surface, a first annular surface, a second annular surface, and a lip surface. The top surface is configured to interface with a drape. The bottom surface is configured to interface with a dressing. The first annular surface is contiguous with the bottom surface and extends orthogonally from the bottom surface towards the top surface. The first annular surface is defined by a first diameter. The second annular surface is contiguous with the top surface and extends orthogonally from the top surface towards the bottom surface. The second annular surface is defined by a second diameter different from the first diameter. The lip surface is contiguous with the first annular surface and the second annular surface.

In some embodiments, the first diameter is less than the second diameter.

In some embodiments, the top surface is substantially disposed along a first plane and the lip surface is substantially disposed along a second plane substantially parallel to the first plane. The bottom surface is substantially disposed along a third plane and a first distance between the first plane and the second plane is less than a second distance between the third plane and the second plane. The bottom surface is substantially disposed along a third plane and a first distance between the first plane and the third plane is between 5 mm and 10 mm, inclusive.

In some embodiments, the bottom surface includes a dimple protruding from the bottom surface.

In some embodiments, the top surface includes a plurality of graduation marks, each of the plurality of graduation marks corresponding with a circumferential location along a perimeter of the top surface.

In some embodiments, the cutting template further includes a hole centered on a center point of the top surface and extending from the top surface through the cutting template to the bottom surface.

In some embodiments, the top surface has a first surface roughness and the bottom surface has a second surface roughness greater than the first surface roughness.

In some embodiments, the cutting template is constructed from a biocompatible polymer.

In some embodiments, the cutting template has a Brinell hardness number of at least 15.

In some embodiments, the cutting template is at least partially transparent.

Another implementation of the present disclosure is a kit for use with a negative pressure wound therapy device. The kit includes a package, a dressing layer, a drape layer, and a cutting template. The package defines a sterilized interior environment. The dressing layer is disposed within the sterilized interior environment. The drape layer is disposed within the sterilized interior environment. The cutting template is disposed within the sterilized interior environment. The cutting template includes a top surface, a bottom surface, and a recess disposed about a perimeter of the cutting template. The recess is configured to receive an edge of a cutting tool.

In some embodiments, the drape layer is sized to cover the top surface and the dressing layer.

In some embodiments, the kit further includes a negative pressure lumen configured to be sealed to the drape layer.

In some embodiments, the drape layer is configured to be cut by the cutting tool when the edge engages the recess and is traversed about the perimeter. The cutting tool may be a scalpel or scissors.

In some embodiments, the top surface is configured to interface with the drape layer and the bottom surface is configured to interface with the dressing layer. The cutting template further includes a first annular surface and a second annular surface. The first annular surface is contiguous with the bottom surface and extends orthogonally from the bottom surface towards the top surface. The second annular surface is contiguous with the top surface and extends orthogonally from the top surface towards the bottom surface. The first annular surface is defined by a first diameter and the second annular surface is defined by a second diameter different from the first diameter.

In some embodiments, the top surface is configured to interface with the drape layer and the bottom surface is configured to interface with the dressing layer. The cutting template further includes a first annular surface and a second annular surface. The first annular surface is contiguous with the bottom surface and extends orthogonally from the bottom surface towards the top surface. The second annular surface is contiguous with the top surface and extends orthogonally from the top surface towards the bottom surface. The cutting template includes a lip surface contiguous with the first annular surface and the second annular surface, the top surface is substantially disposed along a first plane, and the lip surface is substantially disposed along a second plane substantially parallel to the first plane. The first annular surface is defined by a first diameter and the second annular surface is defined by a second diameter greater than the first diameter. The difference between the first diameter and the second diameter is selected such that the drape layer does not contact the second annular surface when the cutting template is placed on the dressing layer and the cutting template is covered by the drape layer. The bottom surface is substantially disposed along a third plane and a first distance between the first plane and the second plane is less than a second distance between the third plane and the second plane. In some embodiments, the bottom surface is substantially disposed along a third plane and a first distance between the first plane and the third plane is between 5 mm and 10 mm, inclusive.

In some embodiments, the bottom surface includes a dimple protruding from the bottom surface. The dressing layer includes a divot configured to receive the dimple.

In some embodiments, the top surface includes a plurality of graduation marks, each of the plurality of graduation marks corresponding with a circumferential location along a perimeter of the top surface.

In some embodiments, the cutting template further includes a hole centered on a center point of the top surface and extending from the top surface through the cutting template to the bottom surface.

In some embodiments, the bottom surface is configured to resist movement of the cutting template along the dressing layer.

In some embodiments, the cutting template is constructed from a biocompatible polymer.

In some embodiments, the cutting template has a Brinell hardness number of at least 15.

In some embodiments, the cutting template is at least partially transparent.

Another implementation of the present disclosure is a method of cutting a drape for use with a negative pressure wound therapy device. The method includes placing a cutting template on a dressing; placing a drape over the cutting template such that the drape covers the cutting template and the dressing; pressing an implement against the drape such that the implement presses the drape towards the cutting template, thereby causing the drape to be cut; rotating, after pressing the implement against the drape such that the implement presses the drape towards the cutting template, the implement about the cutting template thereby causing a cutout to be separated from the drape and an aperture to be simultaneously formed in the drape; removing the cutout from the aperture; and sealing a negative pressure lumen of the negative pressure wound therapy device about the aperture.

In some embodiments, the cutting template is configured such that a gap is formed between the cutting template, the dressing, and the drape proximate an interface between the cutting template and the dressing.

In some embodiments, the cutting template includes a bottom surface, a top surface, a first annular surface, and a second annular surface. The bottom surface is configured to interface with the dressing. The top surface is opposite the bottom surface and configured to interface with the drape. The first annular surface is contiguous with the bottom surface and extends orthogonally from the bottom surface towards the top surface. The second annular surface is contiguous with the top surface and extends orthogonally from the top surface towards the bottom surface. The first annular surface is defined by a first diameter and the second annular surface is defined by a second diameter different from the first diameter. The cutting template includes a lip surface contiguous with the first annular surface and the second annular surface, the top surface is substantially disposed along a first plane, and the lip surface is substantially disposed along a second plane substantially parallel to the first plane.

In some embodiments, the cutting template includes a bottom surface, a top surface, a first annular surface, and a second annular surface. The bottom surface is configured to interface with the dressing. The top surface is opposite the bottom surface and configured to interface with the drape. The first annular surface is contiguous with the bottom surface and extends orthogonally from the bottom surface towards the top surface. The second annular surface is contiguous with the top surface and extends orthogonally from the top surface towards the bottom surface. The first annular surface is defined by a first diameter and the second annular surface is defined by a second diameter different from the first diameter. The difference between the first diameter and the second diameter is selected such that the drape does not contact the second annular surface when the cutting template is placed on the dressing and the cutting template is covered by the drape. The bottom surface is substantially disposed along a third plane and a first distance between the first plane and the second plane is less than a second distance between the third plane and the second plane. The bottom surface is substantially disposed along a third plane and a first distance between the first plane and the third plane is between 2 mm and 10 mm, inclusive.

In some embodiments, the method further includes the step of locating the cutting template on the dressing such that a dimple on the cutting template is received in a divot on the dressing.

In some embodiments, the method further includes the steps of rotating, prior to placing the cutting template on the dressing, the cutting template along a perimeter of a wound bed, and placing, prior to placing the cutting template on the dressing and after rotating the cutting template along the perimeter of the wound bed, the dressing over at least a portion of the wound bed. The cutting template includes a top surface configured to be covered by the drape prior to the implement being pressed against the drape and a plurality of graduation marks disposed along the top surface, where the plurality of graduation marks can be utilized to determine a length of at least a portion of the wound bed. The cutting template further includes a hole centered on a center point of the top surface and extending through the cutting template.

In some embodiments, the cutting template includes a bottom surface configured to interface with the dressing. The bottom surface is configured to resist movement of the cutting template along the dressing.

In some embodiments, the cutting template is constructed from a biocompatible polymer.

In some embodiments, the cutting template has a Brinell hardness number of at least 15.

In some embodiments, the cutting template is cylindrical.

In some embodiments, the cutting template is at least partially transparent.

DETAILED DESCRIPTION

Overview

Figure 1:
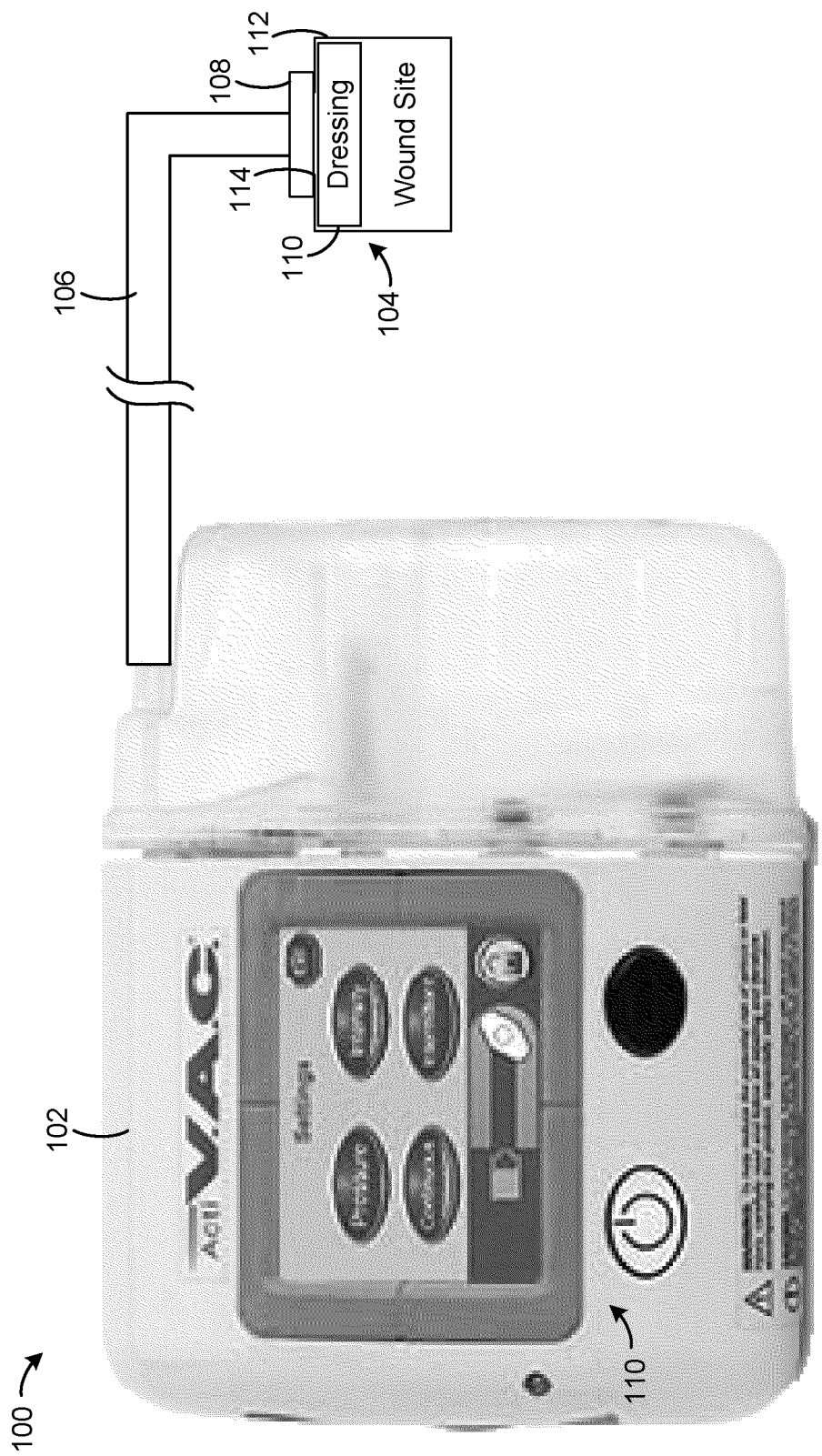
FIG. 1 is a drawing of a negative pressure wound therapy (NPWT) system including a NPWT device fluidly connected with a wound site, according to an exemplary embodiment.
Figure 2:
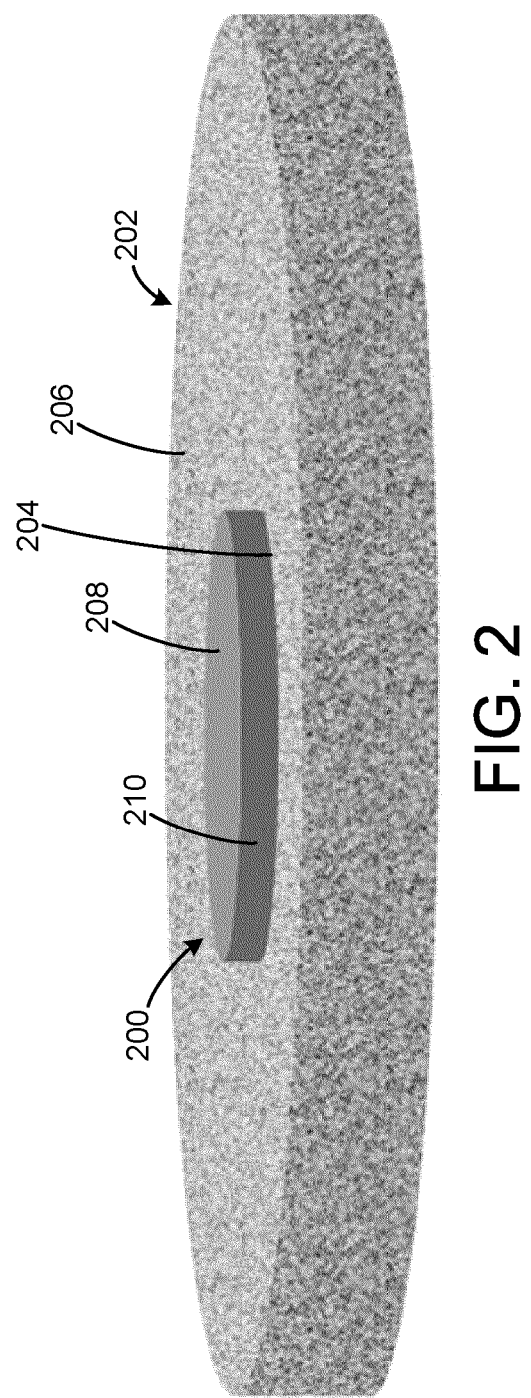
FIG. 2 is a perspective view of a cutting template, placed on a dressing, for use with a NPWT device, according to an exemplary embodiment.
Figure 3:
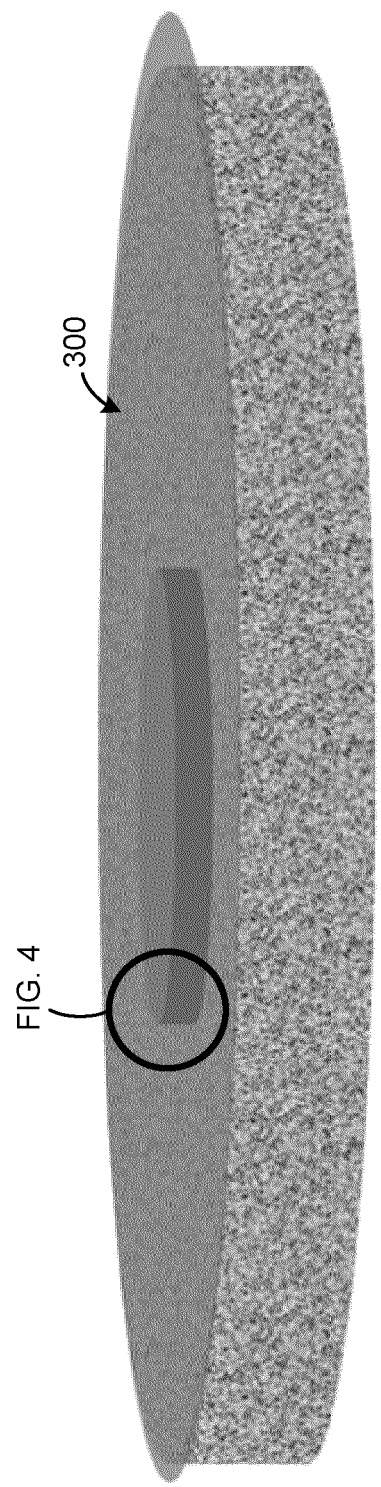
FIG. 3 is a perspective view of a cutting template, placed on a dressing and covered with a drape, for use with a NPWT device, according to an exemplary embodiment.
Figure 4:
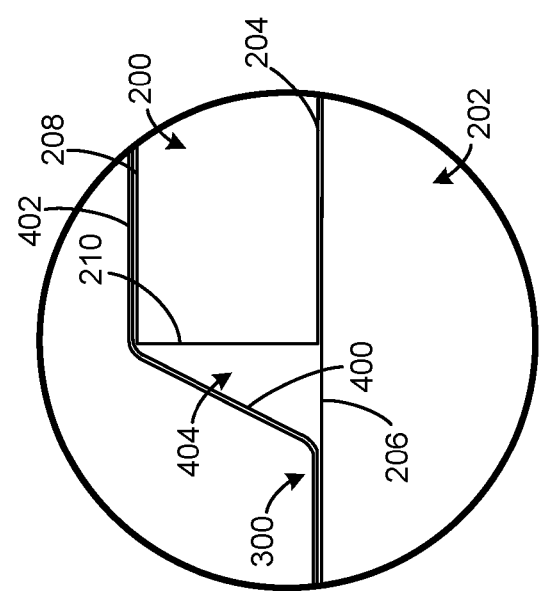
FIG. 4 is a cross-sectional view of a portion of a cutting template, placed on a dressing and covered with a drape, for use with a NPWT device, according to an exemplary embodiment.
Figure 5:
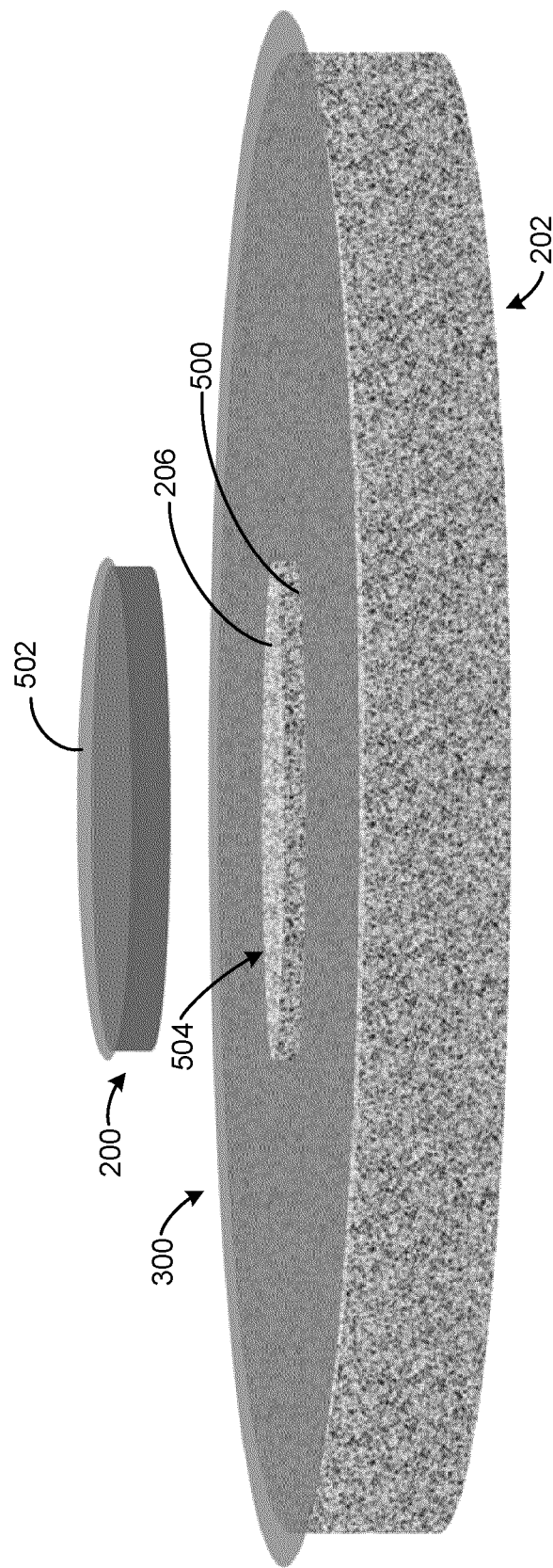
FIG. 5 is a perspective view of a cutting template, removed from a dressing that is covered with a drape, for use with a NPWT device, according to an exemplary embodiment.
Figure 6:
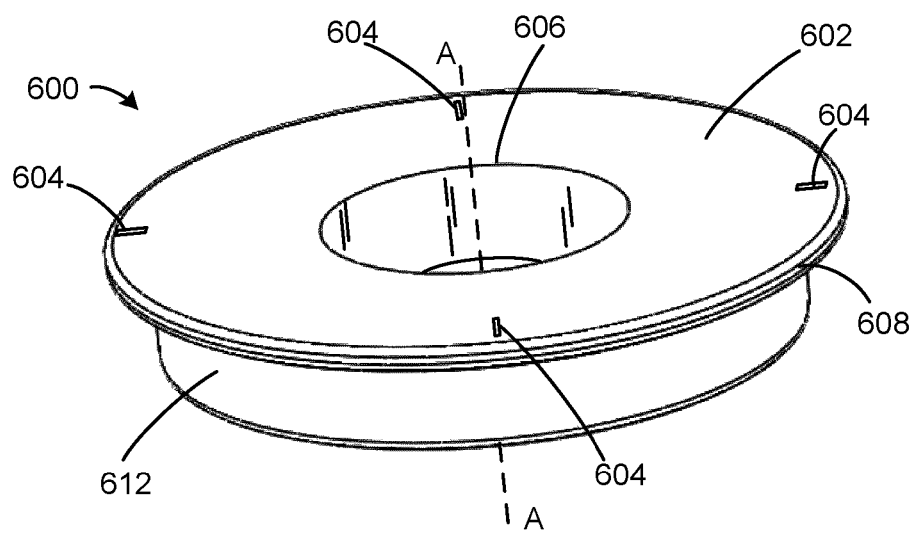
FIG. 6 is a top perspective view of a cutting template for use with a NPWT device, according to an exemplary embodiment.
Figure 7:
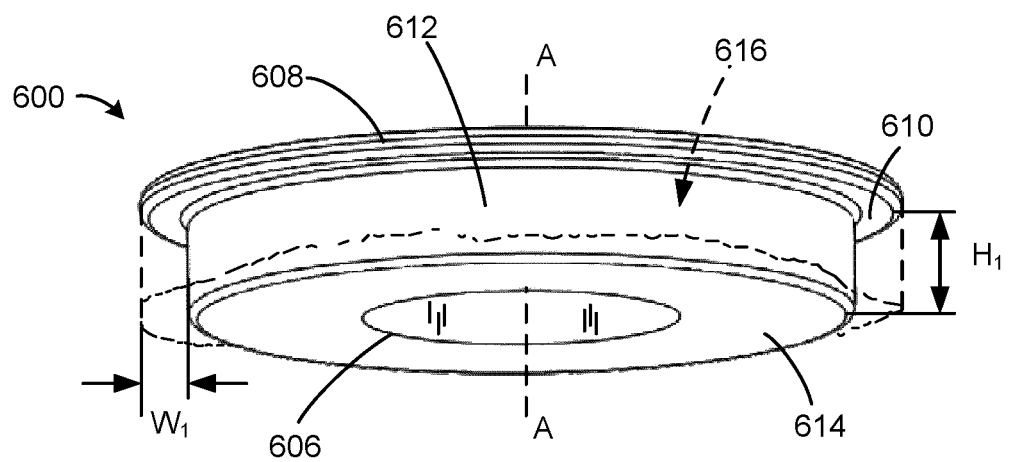
FIG. 7 is a bottom perspective view of the cutting template of FIG. 6, according to an exemplary embodiment.
Figure 8:
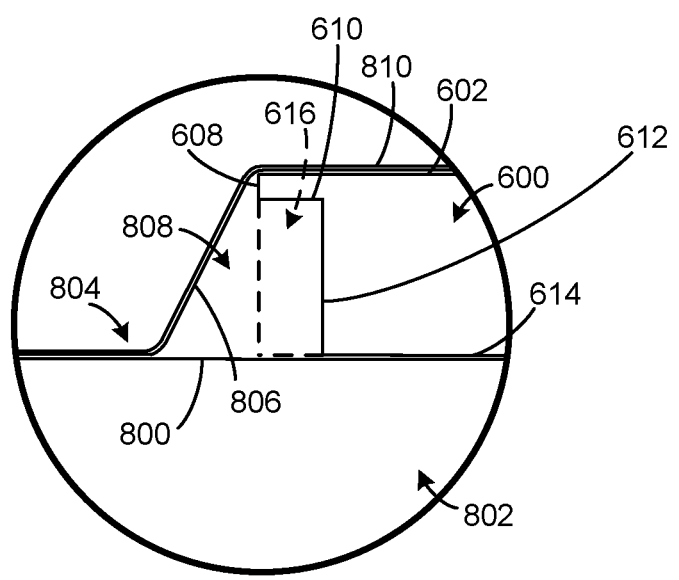
FIG. 8 is a cross-sectional view of a portion of the cutting template of FIG. 6, placed on a dressing and covered with a drape, according to an exemplary embodiment.

Referring generally to the FIGURES, a cutting template for a negative pressure wound therapy (NPWT) device and components thereof is shown, according to various exemplary embodiments. The cutting template is placed on a dressing, which is placed over a tissue wound, and subsequently covered with a drape. The cutting template is configured such that a gap is formed between the dressing, a portion of the cutting template, and the drape. An edge of cutting tool may then be drawn across the drape, opposite the gap, such that the edge is located between the dressing and the cutting template, thereby cutting the drape. After the drape is cut so as to form an aperture in the drape from which the cutting template and a cutout are removed. A manifold may then be sealed to the drape about the aperture, so as to facilitate interaction of the NPWT device with the dressing within the drape. According to any of the embodiments disclosed herein, the cutting template may be formed from a suitable material, such felted or non-felted reticulated open-cell foam material, a plastic material, a rubber material, or other suitable material. The cutting templates of the present disclosure may also include a light adhesive (e.g. tacky, etc.) on the side facing away from the drape, so as to resist movement of the template on the dressing as the cutout is being made.

In some embodiments, the cutting template includes two annular surfaces which are offset so as to form a recess beneath a lip surface. In other embodiments, the cutting template includes a plurality of annular surfaces and a plurality of lip surfaces. These lip surfaces may form a recess along a side of the cutting template. In other embodiments, the cutting template includes two annular surfaces which are offset so as to form a recess above a lip surface.

The cutting template may include a slot extending radially towards a central axis thereof. The slot may facilitate cutting of the drape in a portion of the gap positioned proximate the slot. The cutting template may include a tab protruding from a top surface of the cutting template. The tab may assist a user in removing the cutting template from a dressing (e.g., after a drape has been cut, etc.). Additionally, the tab may facilitate cutting of the drape in a portion of the gap positioned proximate the tab.

The cutting template may include graduation marks positioned along a top surface of the cutting template. The graduation marks may facilitate measurement of a length and width of a tissue wound via rotation of the cutting tool around a tissue wound. The cutting template may include a hole through the center of the cutting template. The hole may facilitate rotation of the cutting template (e.g., around a tissue wound, etc.). The cutting template may include a dimple disposed on a bottom surface thereof. The dimple may facilitate collocation of the cutting template and in a divot in the dressing. These and other features and advantages of the cutting template are described in detail below.

NPWT System

Referring now to FIG. 1, a NPWT system 100 is shown, according to an exemplary embodiment. NPWT system 100 is shown to include a therapy device 102 fluidly connected to a wound site 104 via tubing 106 and a manifold 108. Wound site 104 include a tissue wound, a wound dressing 110 that covers the tissue wound and adheres to a patient's skin, and a drape 112 that covers wound dressing 110 and manifold 108. Drape 112 may adhere to wound dressing 110 and/or the patient's skin. Drape 112 facilitates a pressure differential between wound site 104 and a surrounding atmosphere. Wound dressing 110 may be referred to as being a dressing layer and drape 112 may be referred to as a drape layer.

Therapy device 102 can be configured to provide negative pressure wound therapy by reducing the pressure at wound site 104. Therapy device 102 can draw a vacuum at wound site 104 (relative to atmospheric pressure) by removing wound exudate, air, and other fluids from wound site 104 through manifold 108 and tubing 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 104 may include instillation fluid previously delivered to wound site 104. Instillation fluid can include, for example, a cleansing fluid, a prescribed fluid, a medicated fluid, an antibiotic fluid, or any other type of fluid which can be delivered to wound site 104 during wound treatment. The fluids removed from wound site 104 pass through manifold 108 and then through tubing 106 and may be collected in a canister that is configured to collect wound exudate and other fluids removed from wound site 104. In addition to providing removing exudate, air, and other fluids from wound site 104, tubing 106 may include separate lumens for use by therapy device 102 to measure pressure within wound site 104.

Set Up of a Typical System

When a typical system is set up, a hole or cross shape is cut in a drape directly over a dressing. However, cutting the drape in this fashion often leads to the creation of a hole that is too large or too small for a device placed over the hole, potentially leading to blockage (e.g., a portion of the drape is sucked into the device, etc.) or leaking (e.g., a gap exists between the device and drape, etc.). As a result, these typical systems operate undesirably when the hole is too large or too small. Additionally, cutting the drape directly over the dressing may cause fragments from the dressing to become dislodged therefrom and potentially introduced into a wound site. These fragments may clog or otherwise contaminate the device.

Even after the drape in these typical systems has been cut, it is difficult to remove the cut portion because the drape adheres to the dressing. Typically, a forceps is used to grip the cut portion and attempts are made to separate the cut portion from the dressing. This may be particularly difficult to achieve if the drape is dense or slick. In addition to being time consuming, removing the cut portion can cause further disturbances to the dressing and wound site.

Set Up of a NPWT System Using an Example Cutting Template

Referring now to FIGS. 2-5, a process for setting up a NPWT system using a cutting template 200 is shown, according to an exemplary embodiment. Cutting template 200 may be generally cylindrical. The NPWT system may be set up (e.g., installed, initially configured, etc.) to begin NPWT on a tissue wound. To begin set up of the NPWT system, a dressing 202 is applied over the tissue wound.

Cutting template 200 is then placed on dressing 202 such that a bottom surface 204 of cutting template 200 interfaces with a top surface 206 of dressing 202. Cutting template 200 also includes a top surface 208 opposite bottom surface 204 and an annular surface 210 which is contiguous with both bottom surface 204 and top surface 208.

Next, a drape 300 is placed over cutting template 200 and dressing 202. Drape 300 includes a bottom surface 400 which interfaces with top surface 206 and top surface 208. Drape 300 also includes a top surface 402 opposite bottom surface 400. Bottom surface 400 does not substantially interface with annular surface 210. Accordingly, a gap 404 exists between top surface 206, bottom surface 400, and annular surface 210. Gap 404 may be increased, decreased, and otherwise changed based upon the configuration of annular surface 210. For example, gap 404 is increased if annular surface 210 defines a recess therein.

After drape 300 is placed over cutting template 200 and dressing 202, drape 300 is cut by an edge of a cutting tool. The cutting tool may be, for example, a scalpel, scissors (e.g., safety scissors, etc.), a blade, and other similar implements. The edge of the cutting tool may be pressed on top surface 402 opposite gap 404, such that the edge may cut drape 300 without interfacing with cutting template 200 or dressing 202. In this way, drape 300 may be cut without cutting dressing 202, thereby avoiding dislodging of particles therefrom, and without marring or otherwise damaging cutting template 200, thereby facilitating repeated usage of cutting template 200 (e.g., with a different drape, etc.).

As the cutting tool cuts drape 300, an aperture 500 is formed in drape 300 and a cutout 502 is separated from drape 300. After aperture 500 is formed, a plug 504 of dressing 202 may protrude through (e.g., stick out from, etc.) aperture 500. Cutout 502 may be separated from cutting template 200 and discarded. A manifold, such as manifold 108, is then adhered to drape 300 over aperture 500. For example, the manifold may include a circular bead of adhesive which is applied to drape 300 proximate a perimeter of aperture 500.

108
Second Example Cutting Template for Use with a NPWT System

Referring now to FIGS. 6-9, a cutting template 600 is shown, according to an exemplary embodiment. Cutting template 600 is generally fastener shaped (e.g., mushroom shaped, top hat shaped, plug shaped, etc.) and is generally constructed from portions of two concentric cylinders of different diameters. Cutting template 600 is centered on a central axis A-A. In various embodiments, cutting template 600 is rotationally symmetrical about the central axis A-A.

Cutting template 600 includes a top surface 602 which is configured to interface with a drape, such as drape 300. In various embodiments, top surface 602 includes a plurality of graduation marks 604. Each graduation mark 604 corresponds with an angular location relative to the central axis A-A. Cutting template 600 also includes a hole 606 centered on the central axis A-A and extending through cutting template 600.

Top surface 602 is contiguous with a first annular surface 608. A border between top surface 602 and first annular surface 608 may be beveled, chamfered, rounded, filleted, or otherwise similarly shaped. First annular surface 608 is defined by a circumference. Graduation marks 604 correspond with locations along the circumference of first annular surface 608. For example, one graduation mark 604 may correspond with a starting point, a second graduation mark 604 may correspond with 25% of the circumference of first annular surface 608, a third graduation mark 604 may correspond with 50% of the circumference of first annular surface 608, and a fourth graduation mark 604 may correspond with 75% of the circumference of first annular surface 608. Prior to covering cutting template 600 with a drape, cutting template 600 may be rolled along first annular surface 608 to measure a length along a dressing or a patient's skin using graduation marks 604. To facilitate rolling of cutting template 600, a user's finger or an implement may be placed through or into hole 606. In one example, cutting template 600 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 604 and hole 606 provide cutting template 600 with an additional functionality separate from facilitating cutting of a drape.

First annular surface 608 is contiguous with a lip surface 610. A border between first annular surface 608 and lip surface 610 may be beveled, chamfered, rounded, filleted, or otherwise similarly shaped. Lip surface 610 is contiguous with a second annular surface 612. A border between lip surface 610 and second annular surface 612 may be beveled, chamfered, rounded, filleted, or otherwise similarly shaped. Like first annular surface 608, second annular surface 612 is centered on the central axis A-A. Second annular surface 612 is contiguous with a bottom surface 614. A border between second annular surface 612 and bottom surface 614 may be beveled, chamfered, rounded, filleted, or otherwise similarly shaped. Top surface 602 is substantially disposed along a first plane, lip surface 610 is substantially disposed along a second plane substantially parallel to the first plane, and bottom surface 614 is substantially disposed along a third plane substantially parallel to the first plane.

A recess 616 is formed between a first boundary defined by first annular surface 608, a second boundary defined by lip surface 610, a third boundary defined by second annular surface 612, and a fourth boundary defined by bottom surface 614. First annular surface 608 is defined by a first radius $R_1$ and second annular surface 612 is defined by a second radius $R_2$. In some embodiments, the first radius $R_1$ is approximately 1.91 centimeters (cm). A difference between first radius $R_1$ and second radius $R_2$ is equal to a first width $W_1$ of lip surface 610. Various values for first radius $R_1$ and second radius $R_2$ can be selected such that first width $W_1$ of lip surface 610 can be changed, thereby facilitating changing of recess 616. Additionally, second annular surface 612 is defined by a first height $H_1$ between lip surface 610 and bottom surface 614. In an exemplary embodiment, first height $H_1$ is 8 millimeters (mm). A distance between top surface 602 and lip surface 610 may be configured such that a distance from bottom surface 614 to top surface 602 is between 2 mm and 10 mm, inclusive.

When using cutting template 600 with an NWPT system, cutting template 600 is placed on a top surface 800 of a dressing 802, which is covering a patient's skin. Next, a drape 804 is placed over cutting template 600 and dressing 802. Drape 804 includes a bottom surface 806 which interfaces with top surface 602 and top surface 800, and may at least partially interface with first annular surface 608. However, cutting template 600 is configured such that drape 804 does not substantially interface with lip surface 610 or second annular surface 612. Accordingly, a gap 808 exists between at least lip surface 610, second annular surface 612, top surface 800, and bottom surface 806. Gap 808 may also exist between bottom surface 806 and at least a portion of first annular surface 608. Gap 808 may be increased, decreased, and otherwise changed based upon the configuration of recess 616. For example, gap 808 is increased if first width $W_1$ of lip surface 610 is increased.

Drape 804 also includes a top surface 810 opposite bottom surface 806. After drape 804 is placed over cutting template 600 and dressing 802, drape 804 is cut by an edge of a cutting tool. The cutting tool may be, for example, a scalpel, scissors (e.g., safety scissors, etc.), a blade, and other similar implements. The edge of the cutting tool may be pressed on top surface 810 opposite gap 808, such that the edge may cut drape 804 without interfacing with cutting template 600 or dressing 802. In this way, drape 804 may be cut without cutting dressing 802, thereby avoiding dislodging of particles therefrom, and without marring or otherwise damaging cutting template 600, thereby facilitating repeated usage of cutting template 600 (e.g., with a different drape, etc.).

As the cutting tool cuts drape 804, an aperture is formed in drape 804 and a cutout is separated from drape 804. After the aperture is formed, a plug of dressing 802 may protrude through (e.g., stick out from, etc.) the aperture. The cutout may be separated from cutting template 600 and discarded. A manifold, such as manifold 108, is then adhered to drape 804 over the aperture. For example, the manifold may include a circular bead of adhesive which is applied to drape 804 proximate a perimeter of the aperture.

In an exemplary embodiment, bottom surface 614 is defined by a first surface roughness and top surface 602 is defined by a second surface roughness less than the first surface roughness. The first surface roughness of bottom surface 614 may be selected such that movement of cutting template 600 relative to dressing 802 is resisted. The surface roughness of bottom surface 614 may be related to a static frictional coefficient with dressing 802. For example, the static frictional coefficient of bottom surface 614 with dressing 802 may be less than 0.5. Similarly, the surface roughness of top surface 602 may be related to a static frictional coefficient with drape 804. For example, the static frictional coefficient of top surface 602 with drape 804 may be greater than 0.5.

Third Example Cutting Template for Use with a NPWT System

Figure 9:
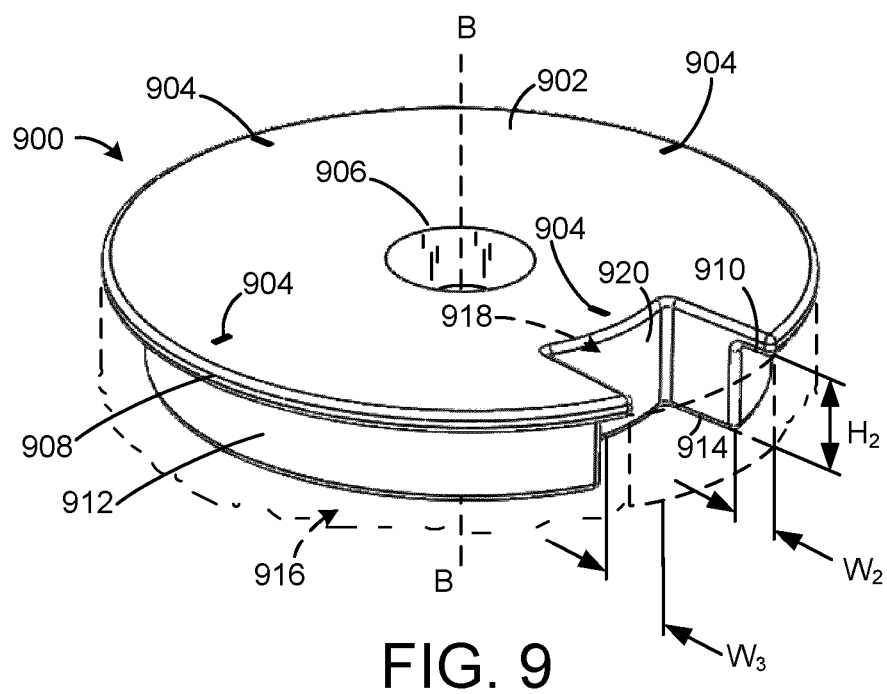
FIG. 9 is a top perspective view of a cutting template for use with a NPWT device, according to an exemplary embodiment.
Figure 10:
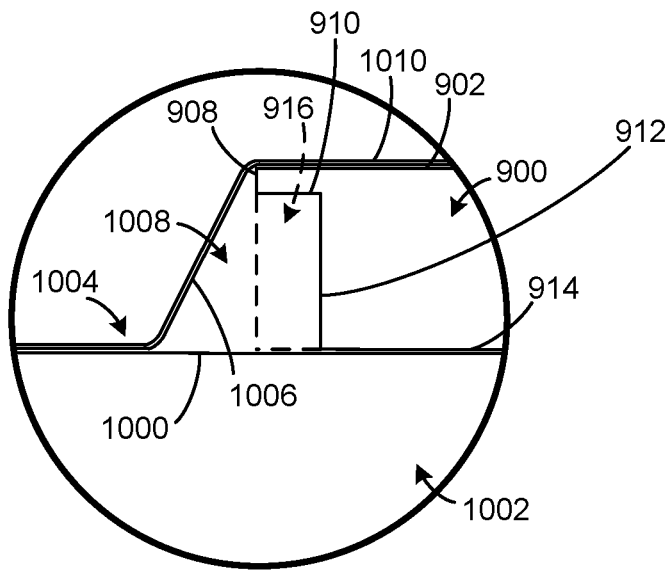
FIG. 10 is a cross-sectional view of a portion of the cutting template of FIG. 9, placed on a dressing and covered with a drape, according to an exemplary embodiment.
Figure 11:
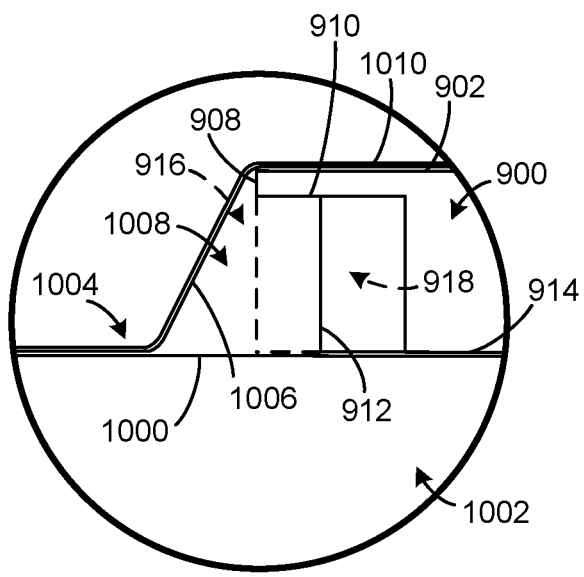
FIG. 11 is a cross-sectional view of another portion of the cutting template of FIG. 9, placed on a dressing and covered with a drape, according to an exemplary embodiment.

Referring now to FIGS. 9-11, a cutting template 900 is shown, according to an exemplary embodiment. Cutting template 900 is generally fastener shaped (e.g., mushroom shaped, top hat shaped, plug shaped, etc.) and is generally constructed from portions of two concentric cylinders of different diameters. Cutting template 900 is centered on a central axis B-B. In various embodiments, cutting template 900 is rotationally symmetrical about the central axis B-B.

Cutting template 900 includes a top surface 902 which is configured to interface with a drape, such as drape 300. In various embodiments, top surface 902 includes a plurality of graduation marks 904. Each graduation mark 904 corresponds with an angular location relative to the central axis B-B. Cutting template 900 also includes a hole 906 centered on the central axis B-B and extending through cutting template 900.

Top surface 902 is contiguous with a first annular surface 908. A border between top surface 902 and first annular surface 908 may be beveled, chamfered, rounded, filleted, or otherwise similarly shaped. First annular surface 908 is defined by a circumference. Graduation marks 904 correspond with locations along the circumference of first annular surface 908. For example, one graduation mark 904 may correspond with a starting point, a second graduation mark 904 may correspond with 25% of the circumference of first annular surface 908, a third graduation mark 904 may correspond with 50% of the circumference of first annular surface 908, and a fourth graduation mark 904 may correspond with 75% of the circumference of first annular surface 908. Prior to covering cutting template 900 with a drape, cutting template 900 may be rolled along first annular surface 908 to measure a length along a dressing or a patient's skin using graduation marks 904. To facilitate rolling of cutting template 900, a user's finger or an implement may be placed through or into hole 906. In one example, cutting template 900 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 904 and hole 906 provide cutting template 900 with an additional functionality separate from facilitating cutting of a drape.

First annular surface 908 is contiguous with a lip surface 910. A border between first annular surface 908 and lip surface 910 may be beveled, chamfered, rounded, filleted, or otherwise similarly shaped. Lip surface 910 is contiguous with a second annular surface 912. A border between lip surface 910 and second annular surface 912 may be beveled, chamfered, rounded, filleted, or otherwise similarly shaped. Like first annular surface 908, second annular surface 912 is centered on the central axis B-B. Second annular surface 912 is contiguous with a bottom surface 914. A border between second annular surface 912 and bottom surface 914 may be beveled, chamfered, rounded, filleted, or otherwise similarly shaped. Top surface 902 is substantially disposed along a first plane, lip surface 910 is substantially disposed along a second plane substantially parallel to the first plane, and bottom surface 914 is substantially disposed along a third plane substantially parallel to the first plane.

A recess 916 is formed between a first boundary defined by first annular surface 908, a second boundary defined by lip surface 910, a third boundary defined by second annular surface 912, and a fourth boundary defined by bottom surface 914. First annular surface 908 is defined by a third radius $R_3$ and second annular surface 912 is defined by a fourth radius $R_4$. A difference between third radius $R_3$ and fourth radius $R_4$ is equal to a second width $W_2$ of lip surface 910. Various values for third radius $R_3$ and fourth radius $R_4$ can be selected such that second width $W_2$ of lip surface 910 can be changed, thereby facilitating changing of recess 916. Additionally, second annular surface 912 is defined by a second height $H_2$ between lip surface 910 and bottom surface 914. In an exemplary embodiment, second height $H_2$ is 8 mm. In another embodiment, second height $H_2$ is 6 mm A distance between top surface 902 and lip surface 910 may be configured such that a distance from bottom surface 914 to top surface 902 is between 2 mm and 10 mm, inclusive.

Cutting template 900 also includes a slot 918. Slot 918 is positioned along a perimeter of cutting template 900 and facilitates the expansion of recess 916 inwards past second annular surface 912 and toward the central axis B-B. In the embodiment shown in FIG. 9, slot 918 is substantially U-shaped (e.g., relative to top surface 902 and bottom surface 914, etc.). However, slot 918 may be substantially V-shaped (e.g., relative to top surface 902 and bottom surface 914, etc.). Slot 918 is defined by a third annular surface 920 offset from second annular surface 912 by a third width $W_3$ greater than second width $W_2$.

When using cutting template 900 with an NWPT system, cutting template 900 is placed on a top surface 1000 of a dressing 1002, which is covering a patient's skin. Next, a drape 1004 is placed over cutting template 900 and dressing 1002. Drape 1004 includes a bottom surface 1006 which interfaces with top surface 902 and top surface 1000, and may at least partially interface with first annular surface 908. However, cutting template 900 is configured such that drape 1004 does not substantially interface with lip surface 910 or second annular surface 912. Accordingly, a gap 1008 exists between at least lip surface 910, second annular surface 912, top surface 1000, and bottom surface 1006. Gap 1008 may also exist between bottom surface 1006 and at least a portion of first annular surface 908. Gap 1008 may be increased, decreased, and otherwise changed based upon the configuration of recess 916. For example, gap 1008 is increased if second width $W_2$ of lip surface 910 is increased.

Drape 1004 also includes a top surface 1010 opposite bottom surface 1006. After drape 1004 is placed over cutting template 900 and dressing 1002, drape 1004 is cut by an edge of a cutting tool. The cutting tool may be, for example, a scalpel, scissors (e.g., safety scissors, etc.), a blade, and other similar implements. The edge of the cutting tool may be pressed on top surface 1010 opposite gap 1008, such that the edge may cut drape 1004 without interfacing with cutting template 900 or dressing 1002. In this way, drape 1004 may be cut without cutting dressing 1002, thereby avoiding dislodging of particles therefrom, and without marring or otherwise damaging cutting template 900, thereby facilitating repeated usage of cutting template 900 (e.g., with a different drape, etc.).

A user may initially cut drape 1004 by pressing the edge of the cutting tool on top surface 1010 opposite slot 918. Gap 1008 is greatest at slot 918 due to third width $W_3$ being greater than second width $W_2$. By pressing the edge of the cutting tool on top surface 1010 opposite slot 918, a user may more easily cut drape 1004. Additionally, this method of cutting drape 1004 decreases a possibility of drape 1004 adhering to cutting template 900, and thereby facilitating more desirable cutting of drape 1004.

As the cutting tool cuts drape 1004, an aperture is formed in drape 1004 and a cutout is separated from drape 1004. After the aperture is formed, a plug of dressing 1002 may protrude through (e.g., stick out from, etc.) the aperture. The cutout may be separated from cutting template 900 and discarded. A manifold, such as manifold 108, is then adhered to drape 1004 over the aperture. For example, the manifold may include a circular bead of adhesive which is applied to drape 1004 proximate a perimeter of the aperture.

In an exemplary embodiment, bottom surface 914 is defined by a first surface roughness and top surface 902 is defined by a second surface roughness less than the first surface roughness. The first surface roughness of bottom surface 914 may be selected such that movement of cutting template 900 relative to dressing 1002 is resisted. The surface roughness of bottom surface 914 may be related to a static frictional coefficient with dressing 1002. For example, the static frictional coefficient of bottom surface 914 with dressing 1002 may be less than 0.5. Similarly, the surface roughness of top surface 902 may be related to a static frictional coefficient with drape 1004. For example, the static frictional coefficient of top surface 902 with drape 1004 may be greater than 0.5.

Fourth Example Cutting Template for Use with a NPWT System

Figure 12:
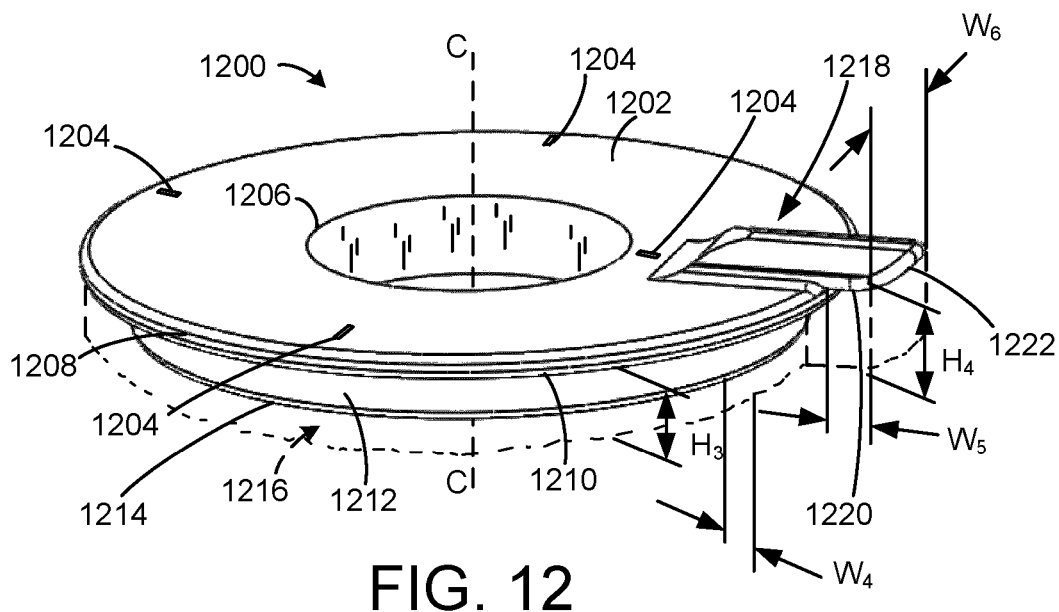
FIG. 12 is a top perspective view of a cutting template for use with a NPWT device, according to an exemplary embodiment.
Figure 13:
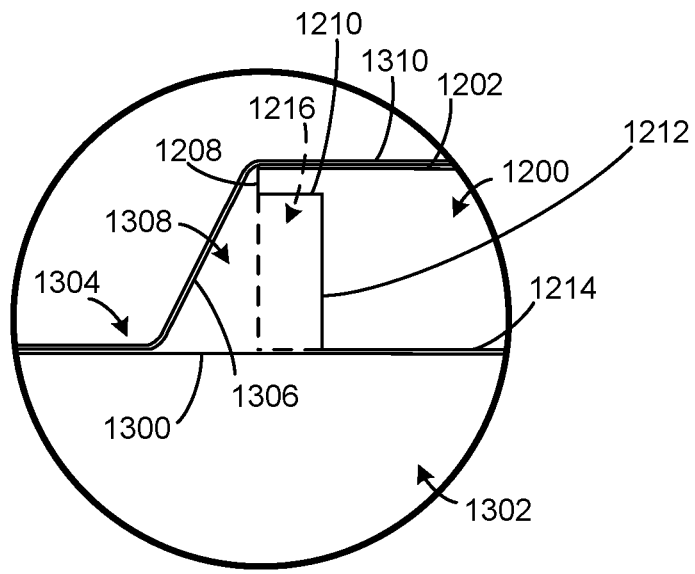
FIG. 13 is a cross-sectional view of a portion of the cutting template of FIG. 12, placed on a dressing and covered with a drape, according to an exemplary embodiment.
Figure 14:
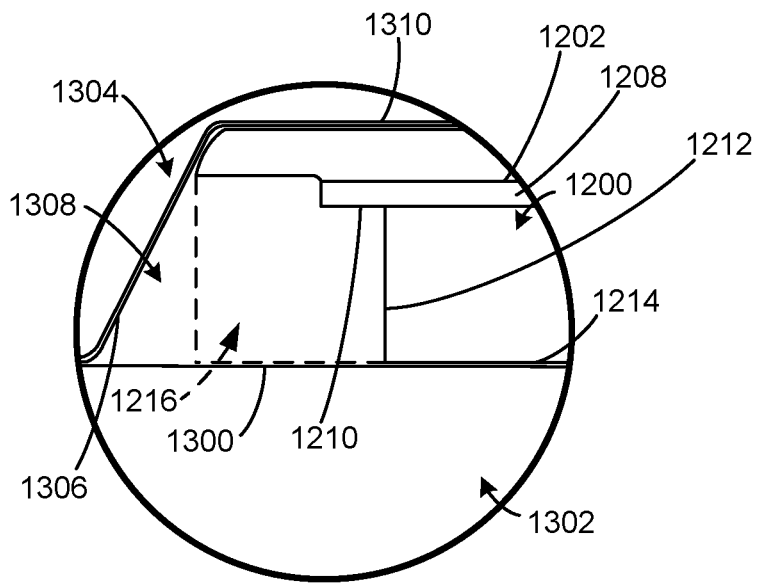
FIG. 14 is a cross-sectional view of another portion of the cutting template of FIG. 12, placed on a dressing and covered with a drape, according to an exemplary embodiment.

Referring now to FIGS. 12-14, a cutting template 1200 is shown, according to an exemplary embodiment. Cutting template 1200 is generally fastener shaped (e.g., mushroom shaped, top hat shaped, plug shaped, etc.) and is generally constructed from portions of two concentric cylinders of different diameters. Cutting template 1200 is centered on a central axis C-C. In various embodiments, cutting template 1200 is rotationally symmetrical about the central axis C-C.

Cutting template 1200 includes a top surface 1202 which is configured to interface with a drape, such as drape 300. In various embodiments, top surface 1202 includes a plurality of graduation marks 1204. Each graduation mark 1204 corresponds with an angular location relative to the central axis C-C. Cutting template 1200 also includes a hole 1206 centered on the central axis C-C and extending through cutting template 1200.

Top surface 1202 is contiguous with a first annular surface 1208. A border between top surface 1202 and first annular surface 1208 may be beveled, chamfered, rounded, filleted, or otherwise similarly shaped. First annular surface 1208 is defined by a circumference. Graduation marks 1204 correspond with locations along the circumference of first annular surface 1208. For example, one graduation mark 1204 may correspond with a starting point, a second graduation mark 1204 may correspond with 25% of the circumference of first annular surface 1208, a third graduation mark 1204 may correspond with 50% of the circumference of first annular surface 1208, and a fourth graduation mark 1204 may correspond with 75% of the circumference of first annular surface 1208. Prior to covering cutting template 1200 with a drape, cutting template 1200 may be rolled along first annular surface 1208 to measure a length along a dressing or a patient's skin using graduation marks 1204. To facilitate rolling of cutting template 1200, a user's finger or an implement may be placed through or into hole 1206. In one example, cutting template 1200 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 1204 and hole 1206 provide cutting template 1200 with an additional functionality separate from facilitating cutting of a drape.

First annular surface 1208 is contiguous with a lip surface 1210. A border between first annular surface 1208 and lip surface 1210 may be beveled, chamfered, rounded, filleted, or otherwise similarly shaped. Lip surface 1210 is contiguous with a second annular surface 1212. A border between lip surface 1210 and second annular surface 1212 may be beveled, chamfered, rounded, filleted, or otherwise similarly shaped. Like first annular surface 1208, second annular surface 1212 is centered on the central axis C-C. Second annular surface 1212 is contiguous with a bottom surface 1214. A border between second annular surface 1212 and bottom surface 1214 may be beveled, chamfered, rounded, filleted, or otherwise similarly shaped. Top surface 1202 is substantially disposed along a first plane, lip surface 1210 is substantially disposed along a second plane substantially parallel to the first plane, and bottom surface 1214 is substantially disposed along a third plane substantially parallel to the first plane.

A recess 1216 is formed between a first boundary defined by first annular surface 1208, a second boundary defined by lip surface 1210, a third boundary defined by second annular surface 1212, and a fourth boundary defined by bottom surface 1214. First annular surface 1208 is defined by a fifth radius $R_5$ and second annular surface 1212 is defined by a sixth radius $R_6$. A difference between fifth radius $R_5$ and sixth radius $R_6$ is equal to a fourth width $W_4$ of lip surface 1210. Various values for fifth radius $R_5$ and sixth radius $R_6$ can be selected such that fourth width $W_4$ of lip surface 1210 can be changed, thereby facilitating changing of recess 1216. Additionally, second annular surface 1212 is defined by a third height $H_3$ between lip surface 1210 and bottom surface 1214. In an exemplary embodiment, third height $H_3$ is 6 mm. In another embodiment, third height $H_3$ is 8 mm. A distance between top surface 1202 and lip surface 1210 may be configured such that a distance from bottom surface 1214 to top surface 1202 is between 2 mm and 10 mm, inclusive.

Cutting template 1200 also includes a tab 1218 (e.g., protrusion, protuberance, etc.). Tab 1218 facilitates easy manipulation (e.g., grabbing, rotating, positioning, grasping, etc.) of cutting template 1200 may a user. For example, tab 1218 may be easily graspable by a user such that cutting template 1200 can be positioned on a dressing. Tab 1218 is positioned along a perimeter of cutting template 900 and facilitates the expansion of recess 1216 outwards past first annular surface 1208 and away from the central axis C-C. In the embodiment shown in FIG. 12, tab 1218 is substantially rectangular. Tab 1218 is defined by a second lip surface 1220. Second lip surface 1220 is defined by a fourth height $H_4$ between second lip surface 1220 and bottom surface 1214. According to various embodiments, fourth height $H_4$ is greater than third height $H_3$. Second lip surface 1220 is also defined by an outer edge 1222 which is contiguous with second lip surface 1220. Second lip surface 1220 is further defined by a fifth width $W_5$ between first annular surface 1208 and outer edge 1222.

When using cutting template 1200 with an NWPT system, cutting template 1200 is placed on a top surface 1300 of a dressing 1302, which is covering a patient's skin. Next, a drape 1304 is placed over cutting template 1200 and dressing 1302. Drape 1304 includes a bottom surface 1306 which interfaces with top surface 1202 and top surface 1300, and may at least partially interface with first annular surface 1208. However, cutting template 1200 is configured such that drape 1304 does not substantially interface with lip surface 1210 or second annular surface 1212. Accordingly, a gap 1308 exists between at least lip surface 1210, second annular surface 1212, top surface 1300, and bottom surface 1306. Gap 1308 may also exist between bottom surface 1306 and at least a portion of first annular surface 1208. Gap 1308 may be increased, decreased, and otherwise changed based upon the configuration of recess 1216. For example, gap 1308 is increased if fifth width $W_5$ of lip surface 1210 is increased.

Drape 1304 also includes a top surface 1310 opposite bottom surface 1306. After drape 1304 is placed over cutting template 1200 and dressing 1302, drape 1304 is cut by an edge of a cutting tool. The cutting tool may be, for example, a scalpel, scissors (e.g., safety scissors, etc.), a blade, and other similar implements. The edge of the cutting tool may be pressed on top surface 1310 opposite gap 1308, such that the edge may cut drape 1304 without interfacing with cutting template 1200 or dressing 1302. In this way, drape 1304 may be cut without cutting dressing 1302, thereby avoiding dislodging of particles therefrom, and without marring or otherwise damaging cutting template 1200, thereby facilitating repeated usage of cutting template 1200 (e.g., with a different drape, etc.).

A user may initially cut drape 1304 by pressing the edge of the cutting tool on top surface 1310 proximate tab 1218. For example, the user may press the edge of the cutting tool on top surface 1310 underneath tab 1218. Gap 1308 is greatest proximate tab 1218 due to tab 1218 protruding from first annular surface 1208. By pressing the edge of the cutting tool on top surface 1310 proximate tab 1218, a user may more easily cut drape 1304. Additionally, this method of cutting drape 1304 decreases a possibility of drape 1304 adhering to cutting template 1200, and thereby facilitating more desirable cutting of drape 1304.

As the cutting tool cuts drape 1304, an aperture is formed in drape 1304 and a cutout is separated from drape 1304. After the aperture is formed, a plug of dressing 1302 may protrude through (e.g., stick out from, etc.) the aperture. The cutout may be separated from cutting template 1200 and discarded. A manifold, such as manifold 108, is then adhered to drape 1304 over the aperture. For example, the manifold may include a circular bead of adhesive which is applied to drape 1304 proximate a perimeter of the aperture.

In an exemplary embodiment, bottom surface 1214 is defined by a first surface roughness and top surface 1202 is defined by a second surface roughness less than the first surface roughness. The first surface roughness of bottom surface 1214 may be selected such that movement of cutting template 1200 relative to dressing 1302 is resisted. The surface roughness of bottom surface 1214 may be related to a static frictional coefficient with dressing 1302. For example, the static frictional coefficient of bottom surface 1214 with dressing 1302 may be less than 0.5. Similarly, the surface roughness of top surface 1202 may be related to a static frictional coefficient with drape 1304. For example, the static frictional coefficient of top surface 1202 with drape 1304 may be greater than 0.5.

Fifth Example Cutting Template for Use with a NPWT System

Figure 15:
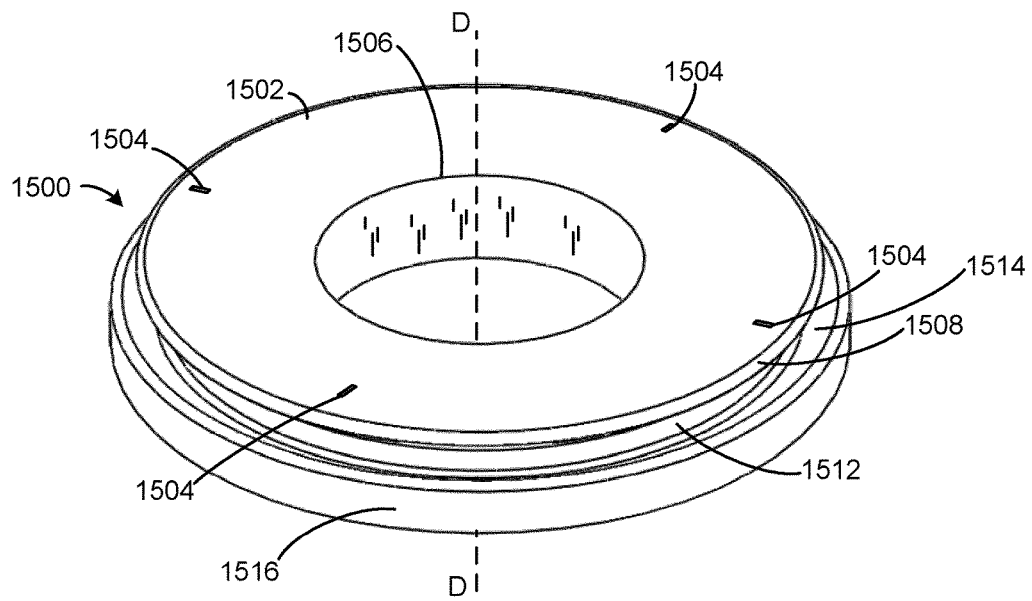
FIG. 15 is a top perspective view of a cutting template for use with a NPWT device, according to an exemplary embodiment.
Figure 16:
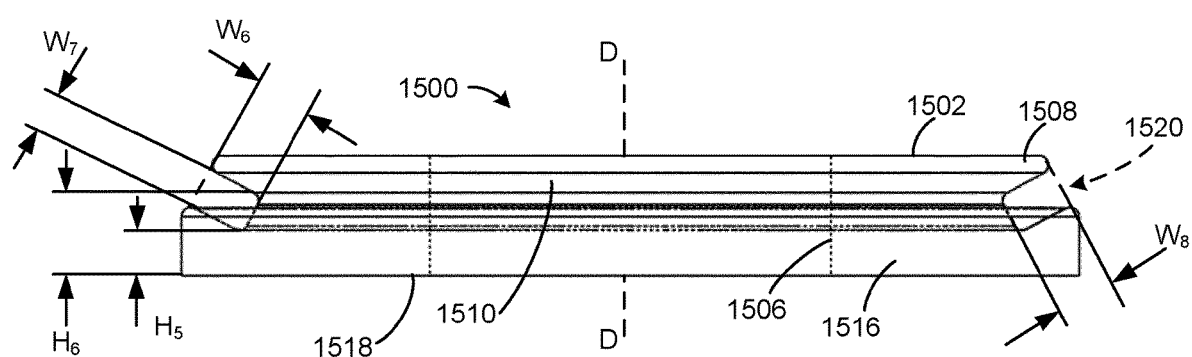
FIG. 16 is a bottom perspective view of the cutting template of FIG. 15, according to an exemplary embodiment.
Figure 17:
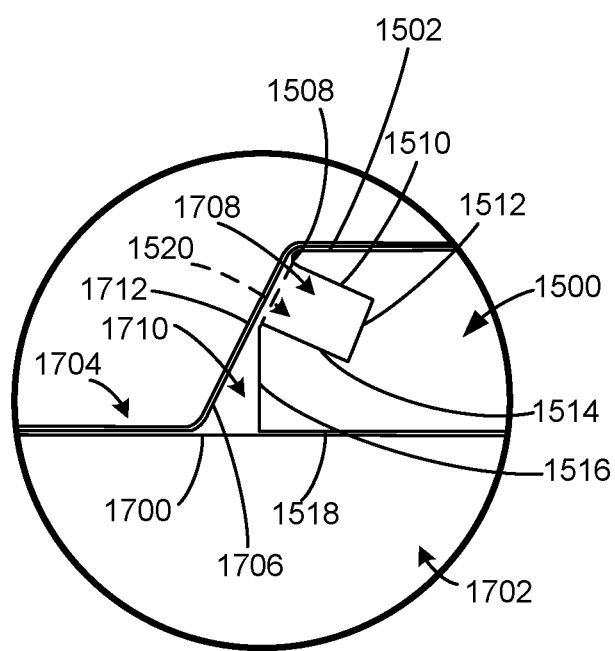
FIG. 17 is a cross-sectional view of a portion of the cutting template of FIG. 15, placed on a dressing and covered with a drape, according to an exemplary embodiment.

Referring now to FIGS. 15-17, a cutting template 1500 is shown, according to an exemplary embodiment. Cutting template 1500 includes a cylindrical bottom portion and a generally frustum-shaped top portion. Cutting template 1500 is centered on a central axis D-D. In various embodiments, cutting template 1500 is rotationally symmetrical about the central axis D-D. FIG. 16 is a cross-section of cutting template 1500 taken about a plane bisecting cutting template 1500 and intersecting the central axis D-D.

Cutting template 1500 includes a top surface 1502 which is configured to interface with a drape, such as drape 300. In various embodiments, top surface 1502 includes a plurality of graduation marks 1504. Each graduation mark 1504 corresponds with an angular location relative to the central axis D-D. Cutting template 1500 also includes a hole 1506 centered on the central axis D-D and extending through cutting template 1500.

Top surface 1502 is contiguous with a first annular surface 1508. A border between top surface 1502 and first annular surface 1508 may be beveled, chamfered, rounded, filleted, or otherwise similarly shaped. As shown in FIG. 15, first annular surface 1508 is rounded. However, first annular surface 1508 may be beveled, chamfered, filleted, or otherwise similarly shaped. Additionally, first annular surface 1508 may include flat portions in addition to any rounded, beveled, chamfered, filleted, or otherwise similar shaped portions.

First annular surface 1508 is contiguous with a first lip surface 1510. A border between first annular surface 1508 and first lip surface 1510 may be beveled, chamfered, rounded, filleted, or otherwise similarly shaped. First lip surface 1510 extends from first annular surface 1508 inwards (e.g., towards the central axis D-D, etc.) and downwards (e.g., away from top surface 1502, etc.).

First lip surface 1510 is contiguous with a second lip surface 1512. A border between first lip surface 1510 and second lip surface 1512 may be beveled, chamfered, rounded, filleted, or otherwise similarly shaped. Second lip surface 1512 extends from first lip surface 1510 outwards (e.g., away from the central axis D-D, etc.) and downwards (e.g., away from top surface 1502, etc.).

Second lip surface 1512 is contiguous with a third lip surface 1514. A border between second lip surface 1512 and third lip surface 1514 may be beveled, chamfered, rounded, filleted, or otherwise similarly shaped. Third lip surface 1514 extends from second lip surface 1512 outwards (e.g., away from the central axis D-D, etc.) and upwards (e.g., towards top surface 1502, etc.).

Third lip surface 1514 is contiguous with a second annular surface 1516. A border between third lip surface 1514 and second annular surface 1516 may be beveled, chamfered, rounded, filleted, or otherwise similarly shaped. Like first annular surface 1508, second annular surface 1516 is centered on the central axis D-D. Second annular surface 1516 is contiguous with a bottom surface 1518. A border between second annular surface 1516 and bottom surface 1518 may be beveled, chamfered, rounded, filleted, or otherwise similarly shaped. Top surface 1502 is substantially disposed along a first plane and bottom surface 1518 is substantially disposed along a second plane substantially parallel to the first plane.

Second annular surface 1516 is defined by a circumference. Graduation marks 1504 correspond with locations along the circumference of second annular surface 1516. For example, one graduation mark 1504 may correspond with a starting point, a second graduation mark 1504 may correspond with 25% of the circumference of second annular surface 1516, a third graduation mark 1504 may correspond with 50% of the circumference of second annular surface 1516, and a fourth graduation mark 1504 may correspond with 75% of the circumference of second annular surface 1516. Prior to covering cutting template 1500 with a drape, cutting template 1500 may be rolled along second annular surface 1516 to measure a length along a dressing or a patient's skin using graduation marks 1504. To facilitate rolling of cutting template 1500, a user's finger or an implement may be placed through or into hole 1506. In one example, cutting template 1500 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 1504 and hole 1506 provide cutting template 1500 with an additional functionality separate from facilitating cutting of a drape.

A recess 1520 is formed between a first boundary defined by first lip surface 1510, a second boundary defined by second lip surface 1512, a third boundary defined by third lip surface 1514, and a fourth boundary defined by a first border between first annular surface 1508 and first lip surface 1510 and a second border between third lip surface 1514 and second annular surface 1516. First lip surface 1510 is defined by a sixth width $W_6$, second lip surface 1512 is defined by a seventh width $W_7$, and third lip surface 1514 is defined by an eighth width $W_8$. In various embodiments, sixth width $W_6$ is approximately equal to eighth width $W_8$. Additionally, first annular surface 1508 is defined by a seventh radius $R_7$ and second annular surface 1516 is defined by an eighth radius $R_8$ greater than seventh radius $R_7$. Various values for sixth width $W_6$, seventh width $W_7$, eighth width $W_8$, seventh radius $R_7$, and eighth radius $R_8$ can be selected to facilitate changing of recess 1520. Additionally, second lip surface 1512 is defined by a fifth height $H_5$ between (i) a boundary between second lip surface 1512 and first lip surface 1510 and (ii) bottom surface 1518. Second lip surface 1512 is also defined by a sixth height $H_6$ between (i) a boundary between second lip surface 1512 and third lip surface 1514 and (ii) bottom surface 1518. In various embodiments, one of fifth height $H_5$ and sixth height $H_6$ is 8 mm. In some embodiments, one of fifth height $H_5$ and sixth height $H_6$ is 6 mm. A distance between top surface 1502 and a boundary between a boundary between second lip surface 1512 and third lip surface 1514 may be configured such that a distance from bottom surface 1518 to top surface 1502 is between 5 mm and 10 mm, inclusive.

When using cutting template 1500 with an NWPT system, cutting template 1500 is placed on a top surface 1700 of a dressing 1702, which is covering a patient's skin. Next, a drape 1704 is placed over cutting template 1500 and dressing 1702. Drape 1704 includes a bottom surface 1706 which interfaces with top surface 1502 and top surface 1700, and may at least partially interface with first annular surface 1508.

Cutting template 1500 is configured such that drape 1704 does not substantially interface with first lip surface 1510, second lip surface 1512, or third lip surface 1514. Accordingly, a first gap 1708 exists between at least first lip surface 1510, second lip surface 1512, or third lip surface 1514. First gap 1708 may be increased, decreased, and otherwise changed based upon the configuration of recess 1520. For example, first gap 1708 is increased if sixth width $W_6$, seventh width $W_7$, or eighth width $W_8$ is increased.

Additionally, cutting template 1500 is configured such that drape 1704 does not substantially interface with at least a portion of second annular surface 1516. Accordingly, a second gap 1710 exists between at least a portion of second annular surface 1516, top surface 1700, and bottom surface 1706. Second gap 1710 may be increased, decreased, and otherwise changed based upon the configuration of recess 1520.

Drape 1704 also includes a top surface 1712 opposite bottom surface 1706. After drape 1704 is placed over cutting template 1500 and dressing 1702, drape 1704 is cut by an edge of a cutting tool. The cutting tool may be, for example, a scalpel, scissors (e.g., safety scissors, etc.), a blade, and other similar implements. The edge of the cutting tool may be pressed on top surface 1712 opposite first gap 1708, such that the edge may cut drape 1704 without interfacing with cutting template 1500 or dressing 1702. As drape 1704 is cut, the edge of the cutting tool may be positioned between first lip surface 1510 and third lip surface 1514, and may be positioned adjacent second lip surface 1512. In this way, drape 1704 may be cut without cutting dressing 1702, thereby avoiding dislodging of particles therefrom, and without marring or otherwise damaging cutting template 1500, thereby facilitating repeated usage of cutting template 1500 (e.g., with a different drape, etc.). Second gap 1710 may minimize adherence of drape 1704 to cutting template 1500, thereby facilitating more desirable cutting of drape 1704.

In some embodiments, first lip surface 1510, second lip surface 1512, and third lip surface 1514 are configured such that recess 1520 is configured to receive an edge of a target cutting tool. For example, cutting template 1500 may be specifically configured to receive an edge of a scalpel.

As the cutting tool cuts drape 1704, an aperture is formed in drape 1704 and a cutout is separated from drape 1704. After the aperture is formed, a plug of dressing 1702 may protrude through (e.g., stick out from, etc.) the aperture. The cutout may be separated from cutting template 1500 and discarded. A manifold, such as manifold 108, is then adhered to drape 1704 over the aperture. For example, the manifold may include a circular bead of adhesive which is applied to drape 1704 proximate a perimeter of the aperture.

In an exemplary embodiment, bottom surface 1518 is defined by a first surface roughness and top surface 1502 is defined by a second surface roughness less than the first surface roughness. The first surface roughness of bottom surface 1518 may be selected such that movement of cutting template 1500 relative to dressing 1702 is resisted. The surface roughness of bottom surface 1518 may be related to a static frictional coefficient with dressing 1702. For example, the static frictional coefficient of bottom surface 1518 with dressing 1702 may be less than 0.5. Similarly, the surface roughness of top surface 1502 may be related to a static frictional coefficient with drape 1704. For example, the static frictional coefficient of top surface 1502 with drape 1704 may be greater than 0.5.

Sixth Example Cutting Template for Use with a NPWT System

Figure 18:
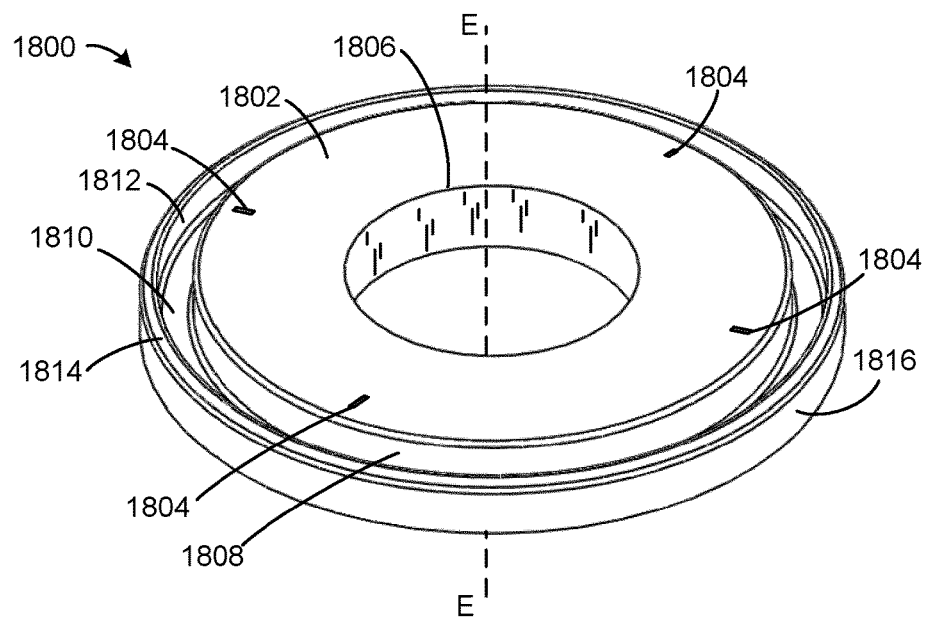
FIG. 18 is a top perspective view of a cutting template for use with a NPWT device, according to an exemplary embodiment.
Figure 19:
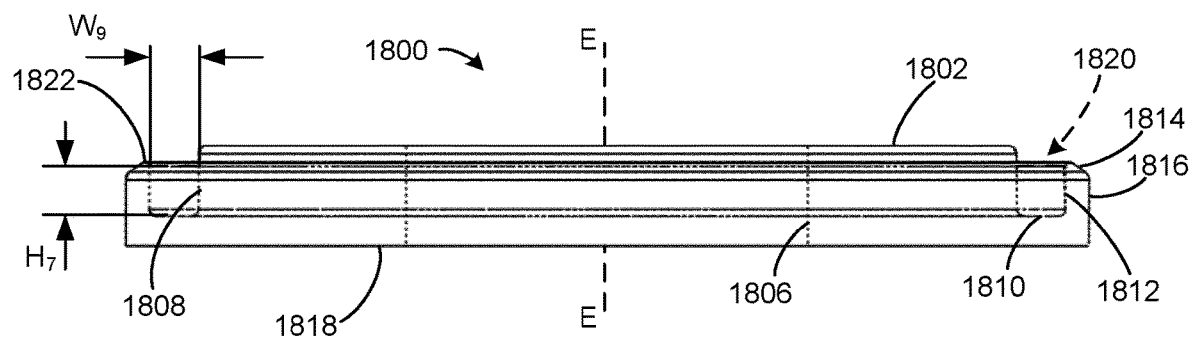
FIG. 19 is a bottom perspective view of the cutting template of FIG. 18, according to an exemplary embodiment.
Figure 20:
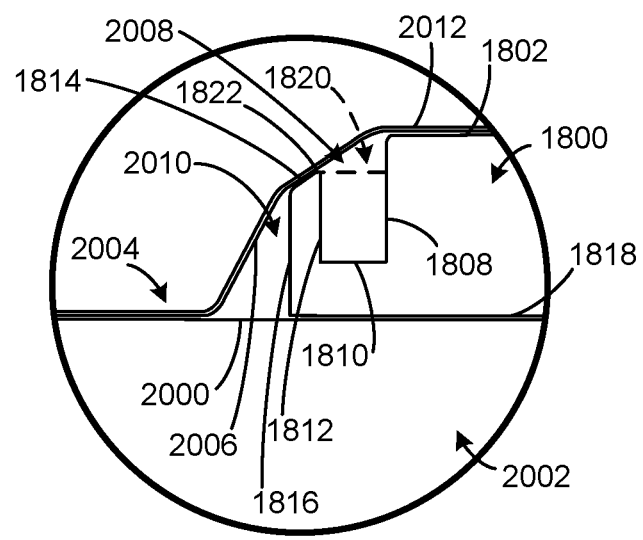
FIG. 20 is a cross-sectional view of a portion of the cutting template of FIG. 18, placed on a dressing and covered with a drape, according to an exemplary embodiment.

Referring now to FIGS. 18-20, a cutting template 1800 is shown, according to an exemplary embodiment. Cutting template 1800 is generally fastener shaped (e.g., mushroom shaped, top hat shaped, plug shaped, etc.) and is generally constructed from portions of two concentric cylinders of different diameters. Cutting template 1800 is centered on a central axis E-E. In various embodiments, cutting template 1800 is rotationally symmetrical about the central axis E-E. FIG. 19 is a cross-section of cutting template 1800 taken about a plane bisecting cutting template 1800 and intersecting the central axis E-E.

Cutting template 1800 includes a top surface 1802 which is configured to interface with a drape, such as drape 300. In various embodiments, top surface 1802 includes a plurality of graduation marks 1804. Each graduation mark 1804 corresponds with an angular location relative to the central axis E-E. Cutting template 1800 also includes a hole 1806 centered on the central axis E-E and extending through cutting template 1800.

Top surface 1802 is contiguous with a first annular surface 1808. A border between top surface 1802 and first annular surface 1808 may be beveled, chamfered, rounded, filleted, or otherwise similarly shaped. First annular surface 1808 is contiguous with a first lip surface 1810. A border between first annular surface 1808 and first lip surface 1810 may be beveled, chamfered, rounded, filleted, or otherwise similarly shaped. First lip surface 1810 extends from first annular surface 1808 outwards (e.g., away from the central axis E-E, etc.). In various embodiments, first lip surface 1810 extends substantially orthogonally from first annular surface 1808. In some embodiments, first lip surface 1810 is disposed along a first plane which is substantially parallel to a second plane upon which top surface 1802 is disposed along.

First lip surface 1810 is contiguous with a second annular surface 1812. A border between first lip surface 1810 and second annular surface 1812 may be beveled, chamfered, rounded, filleted, or otherwise similarly shaped. Second annular surface 1812 extends from first lip surface 1810 towards a plane upon which top surface 1802 is disposed. In various embodiments, second annular surface 1812 extends orthogonally from first lip surface 1810. In some embodiments, second annular surface 1812 is substantially concentric with first annular surface 1808.

Second annular surface 1812 is contiguous with a second lip surface 1814. A border between second annular surface 1812 and second lip surface 1814 may be beveled, chamfered, rounded, filleted, or otherwise similarly shaped. As shown in FIG. 18, second lip surface 1814 is rounded. However, second lip surface 1814 may be beveled, chamfered, filleted, or otherwise similarly shaped. Additionally, second lip surface 1814 may include flat portions in addition to any rounded, beveled, chamfered, filleted, or otherwise similar shaped portions. Second lip surface 1814 extends from second annular surface 1812 outwards (e.g., away from the central axis E-E, etc.).

Second lip surface 1814 is contiguous with a third annular surface 1816. A border between second lip surface 1814 and third annular surface 1816 may be beveled, chamfered, rounded, filleted, or otherwise similarly shaped. Third annular surface 1816 extends from second lip surface 1814 away from a plane upon which top surface 1802 is disposed. In some embodiments, third annular surface 1816 is substantially concentric with first annular surface 1808. Third annular surface 1816 is contiguous with a bottom surface 1818. A border between third annular surface 1816 and bottom surface 1818 may be beveled, chamfered, rounded, filleted, or otherwise similarly shaped. Top surface 1802 is substantially disposed along a first plane and bottom surface 1818 is substantially disposed along a second plane substantially parallel to the first plane.

Third annular surface 1816 is defined by a circumference. Graduation marks 1804 correspond with locations along the circumference of third annular surface 1816. For example, one graduation mark 1804 may correspond with a starting point, a second graduation mark 1804 may correspond with 25% of the circumference of third annular surface 1816, a third graduation mark 1804 may correspond with 50% of the circumference of third annular surface 1816, and a fourth graduation mark 1804 may correspond with 75% of the circumference of third annular surface 1816. Prior to covering cutting template 1800 with a drape, cutting template 1800 may be rolled along third annular surface 1816 to measure a length along a dressing or a patient's skin using graduation marks 1804. To facilitate rolling of cutting template 1800, a user's finger or an implement may be placed through or into hole 1806. In one example, cutting template 1800 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 1804 and hole 1806 provide cutting template 1800 with an additional functionality separate from facilitating cutting of a drape.

A recess 1820 is formed between a first boundary defined by first annular surface 1808, the first lip surface 1810, the second annular surface 1812, and a fourth boundary defined between the second lip surface 1814 and the first annular surface 1808. First lip surface 1810 is defined by a ninth width $W_9$. Additionally, first annular surface 1808 is defined by a ninth radius $R_9$ and third annular surface 1816 is defined by a tenth radius $R_{10}$ greater than ninth radius $R_9$. Various values for ninth radius $R_9$ and tenth radius $R_{10}$ can be selected to facilitate changing of ninth width $W_9$. Additionally, second lip surface 1814 is defined by a seventh height $H_7$ between a top edge 1822 of second lip surface 1814 and first lip surface 1810. In various embodiments, seventh height $H_7$ is 8 mm. In some embodiments, seventh height $H_7$ is 6 mm. A distance between top surface 1802 and top edge 1822 may be configured such that a distance from bottom surface 1818 to top surface 1802 is between 2 mm and 10 mm, inclusive.

When using cutting template 1800 with an NWPT system, cutting template 1800 is placed on a top surface 2000 of a dressing 2002, which is covering a patient's skin. Next, a drape 2004 is placed over cutting template 1800 and dressing 2002. Drape 2004 includes a bottom surface 2006 which interfaces with top surface 1802 and top surface 2000, and may at least partially interface with second lip surface 1814 (e.g., with top edge 1822, etc.).

Cutting template 1800 is configured such that drape 2004 does not substantially interface with first annular surface 1808, first lip surface 1810, second annular surface 1812, or third annular surface 1816. Accordingly, a first gap 2008 exists between at least first annular surface 1808, first lip surface 1810, and second annular surface 1812. First gap 2008 may be increased, decreased, and otherwise changed based upon the configuration of recess 1820. For example, first gap 2008 is increased if ninth width $W_9$ or seventh height $H_7$ is increased.

Additionally, cutting template 1800 is configured such that drape 2004 does not substantially interface with at least a portion of third annular surface 1816. Accordingly, a second gap 2010 exists between at least a portion of third annular surface 1816, top surface 2000, and bottom surface 2006. Second gap 2010 may be increased, decreased, and otherwise changed based upon the configuration of recess 1820.

Drape 2004 also includes a top surface 2012 opposite bottom surface 2006. After drape 2004 is placed over cutting template 1800 and dressing 2002, drape 2004 is cut by an edge of a cutting tool. The cutting tool may be, for example, a scalpel, scissors (e.g., safety scissors, etc.), a blade, and other similar implements. The edge of the cutting tool may be pressed on top surface 2012 opposite first gap 2008, such that the edge may cut drape 2004 without interfacing with cutting template 1800 or dressing 2002. As drape 2004 is cut, the edge of the cutting tool may be positioned between first annular surface 1808 and the second annular surface 1812, and may be positioned adjacent first lip surface 1810. In this way, drape 2004 may be cut without cutting dressing 2002, thereby avoiding dislodging of particles therefrom, and without marring or otherwise damaging cutting template 1800, thereby facilitating repeated usage of cutting template 1800 (e.g., with a different drape, etc.). Second gap 2010 may minimize adherence of drape 2004 to cutting template 1800, thereby facilitating more desirable cutting of drape 2004.

In some embodiments, first annular surface 1808, first lip surface 1810, and second annular surface 1812 are configured such that recess 1820 is configured to receive an edge of a target cutting tool. For example, cutting template 1800 may be specifically configured to receive an edge of a scalpel.

As the cutting tool cuts drape 2004, an aperture is formed in drape 2004 and a cutout is separated from drape 2004. After the aperture is formed, a plug of dressing 2002 may protrude through (e.g., stick out from, etc.) the aperture. The cutout may be separated from cutting template 1800 and discarded. A manifold, such as manifold 108, is then adhered to drape 2004 over the aperture. For example, the manifold may include a circular bead of adhesive which is applied to drape 2004 proximate a perimeter of the aperture.

In an exemplary embodiment, bottom surface 1818 is defined by a first surface roughness and top surface 1802 is defined by a second surface roughness less than the first surface roughness. The first surface roughness of bottom surface 1818 may be selected such that movement of cutting template 1800 relative to dressing 2002 is resisted. The surface roughness of bottom surface 1818 may be related to a static frictional coefficient with dressing 2002. For example, the static frictional coefficient of bottom surface 1818 with dressing 2002 may be less than 0.5. Similarly, the surface roughness of top surface 1802 may be related to a static frictional coefficient with drape 2004. For example, the static frictional coefficient of top surface 1802 with drape 2004 may be greater than 0.5.

Seventh Example Cutting Template for Use with a NPWT System

Figure 21:
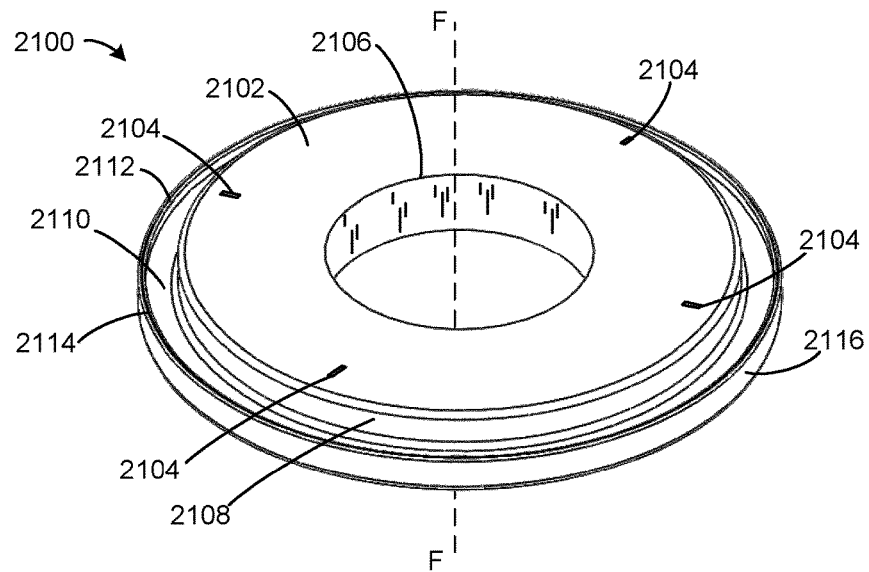
FIG. 21 is a top perspective view of a cutting template for use with a NPWT device, according to an exemplary embodiment.
Figure 22:
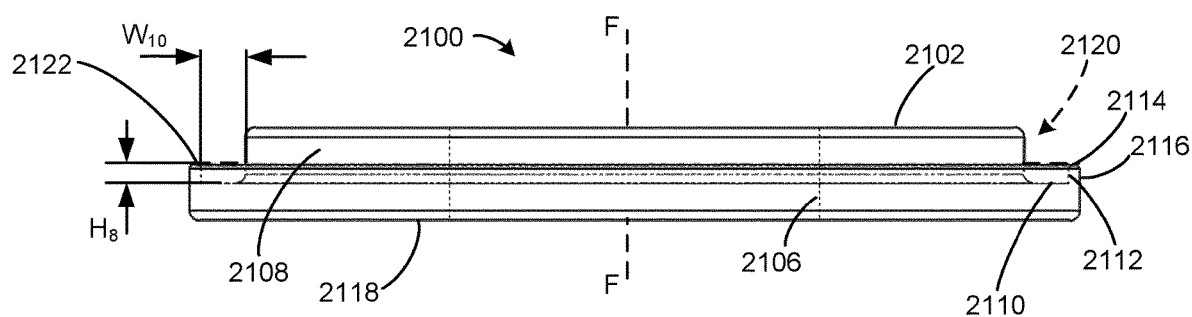
FIG. 22 is a bottom perspective view of the cutting template of FIG. 21, according to an exemplary embodiment.
Figure 23:
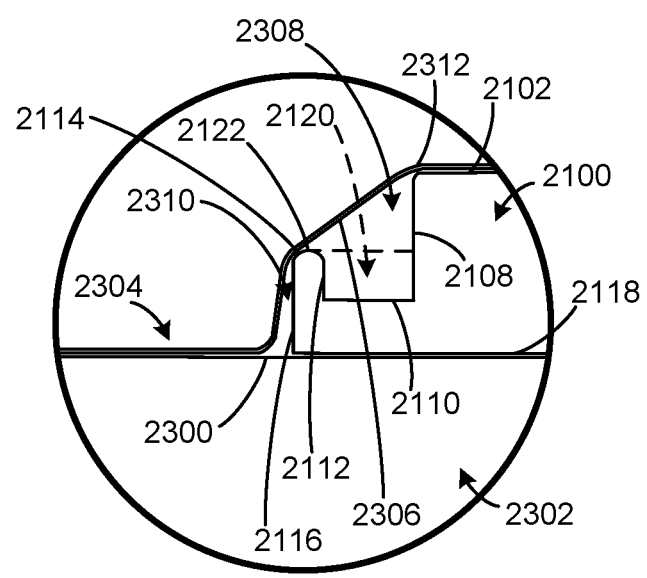
FIG. 23 is a cross-sectional view of a portion of the cutting template of FIG. 21, placed on a dressing and covered with a drape, according to an exemplary embodiment.

Referring now to FIGS. 21-23, a cutting template 2100 is shown, according to an exemplary embodiment. Cutting template 2100 is generally fastener shaped (e.g., mushroom shaped, top hat shaped, plug shaped, etc.) and is generally constructed from portions of two concentric cylinders of different diameters. Cutting template 2100 is centered on a central axis F-F. In various embodiments, cutting template 2100 is rotationally symmetrical about the central axis F-F. FIG. 22 is a cross-section of cutting template 2100 taken about a plane bisecting cutting template 2100 and intersecting the central axis F-F.

Cutting template 2100 includes a top surface 2102 which is configured to interface with a drape, such as drape 300. In various embodiments, top surface 2102 includes a plurality of graduation marks 2104. Each graduation mark 2104 corresponds with an angular location relative to the central axis F-F. Cutting template 2100 also includes a hole 2106 centered on the central axis F-F and extending through cutting template 2100.

Top surface 2102 is contiguous with a first annular surface 2108. A border between top surface 2102 and first annular surface 2108 may be beveled, chamfered, rounded, filleted, or otherwise similarly shaped. First annular surface 2108 is contiguous with a first lip surface 2110. A border between first annular surface 2108 and first lip surface 2110 may be beveled, chamfered, rounded, filleted, or otherwise similarly shaped. First lip surface 2110 extends from first annular surface 2108 outwards (e.g., away from the central axis F-F, etc.). In various embodiments, first lip surface 2110 extends substantially orthogonally from first annular surface 2108. In some embodiments, first lip surface 2110 is disposed along a first plane which is substantially parallel to a second plane upon which top surface 2102 is disposed along.

First lip surface 2110 is contiguous with a second annular surface 2112. A border between first lip surface 2110 and second annular surface 2112 may be beveled, chamfered, rounded, filleted, or otherwise similarly shaped. Second annular surface 2112 extends from first lip surface 2110 towards a plane upon which top surface 2102 is disposed. In various embodiments, second annular surface 2112 extends orthogonally from first lip surface 2110. In some embodiments, second annular surface 2112 is substantially concentric with first annular surface 2108.

Second annular surface 2112 is contiguous with a second lip surface 2114. A border between second annular surface 2112 and second lip surface 2114 may be beveled, chamfered, rounded, filleted, or otherwise similarly shaped. As shown in FIG. 21, second lip surface 2114 is rounded. However, second lip surface 2114 may be beveled, chamfered, filleted, or otherwise similarly shaped. Additionally, second lip surface 2114 may include flat portions in addition to any rounded, beveled, chamfered, filleted, or otherwise similar shaped portions. Second lip surface 2114 extends from second annular surface 2112 outwards (e.g., away from the central axis F-F, etc.).

Second lip surface 2114 is contiguous with a third annular surface 2116. A border between second lip surface 2114 and third annular surface 2116 may be beveled, chamfered, rounded, filleted, or otherwise similarly shaped. Third annular surface 2116 extends from second lip surface 2114 away from a plane upon which top surface 2102 is disposed. In some embodiments, third annular surface 2116 is substantially concentric with first annular surface 2108. Third annular surface 2116 is contiguous with a bottom surface 2118. A border between third annular surface 2116 and bottom surface 2118 may be beveled, chamfered, rounded, filleted, or otherwise similarly shaped. Top surface 2102 is substantially disposed along a first plane and bottom surface 2118 is substantially disposed along a second plane substantially parallel to the first plane.

Third annular surface 2116 is defined by a circumference. Graduation marks 2104 correspond with locations along the circumference of third annular surface 2116. For example, one graduation mark 2104 may correspond with a starting point, a second graduation mark 2104 may correspond with 25% of the circumference of third annular surface 2116, a third graduation mark 2104 may correspond with 50% of the circumference of third annular surface 2116, and a fourth graduation mark 2104 may correspond with 75% of the circumference of third annular surface 2116. Prior to covering cutting template 2100 with a drape, cutting template 2100 may be rolled along third annular surface 2116 to measure a length along a dressing or a patient's skin using graduation marks 2104. To facilitate rolling of cutting template 2100, a user's finger or an implement may be placed through or into hole 2106. In one example, cutting template 2100 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 2104 and hole 2106 provide cutting template 2100 with an additional functionality separate from facilitating cutting of a drape.

A recess 2120 is formed between a first boundary defined by first annular surface 2108, the first lip surface 2110, the second annular surface 2112, and a fourth boundary defined between the second lip surface 2114 and the first annular surface 2108. First lip surface 2110 is defined by a tenth width $W_{10}$. Additionally, first annular surface 2108 is defined by an eleventh radius $R_{11}$ and third annular surface 2116 is defined by a twelfth radius $R_{12}$ greater than eleventh radius $R_{11}$. Various values for eleventh radius $R_{11}$ and twelfth radius $R_{12}$ can be selected to facilitate changing of tenth width $W_{10}$. Additionally, second lip surface 2114 is defined by an eighth height $H_8$ between a top edge 2122 of second lip surface 2114 and first lip surface 2110. In various embodiments, eighth height $H_8$ is 8 mm. In some embodiments, eighth height $H_8$ is 6 mm. A distance between top surface 2102 and top edge 2122 may be configured such that a distance from bottom surface 2118 to top surface 2102 is between 2 mm and 10 mm, inclusive.

When using cutting template 2100 with an NWPT system, cutting template 2100 is placed on a top surface 2300 of a dressing 2302, which is covering a patient's skin. Next, a drape 2304 is placed over cutting template 2100 and dressing 2302. Drape 2304 includes a bottom surface 2306 which interfaces with top surface 2102 and top surface 2300, and may at least partially interface with second lip surface 2114 (e.g., with top edge 2122, etc.).

Cutting template 2100 is configured such that drape 2304 does not substantially interface with first annular surface 2108, first lip surface 2110, second annular surface 2112, or third annular surface 2116. Accordingly, a first gap 2308 exists between at least first annular surface 2108, first lip surface 2110, and second annular surface 2112. First gap 2308 may be increased, decreased, and otherwise changed based upon the configuration of recess 2120. For example, first gap 2308 is increased if tenth width $W_{10}$ or eighth height $H_8$ is increased.

Additionally, cutting template 2100 is configured such that drape 2304 does not substantially interface with at least a portion of third annular surface 2116. Accordingly, a second gap 2310 exists between at least a portion of third annular surface 2116, top surface 2300, and bottom surface 2306. Second gap 2310 may be increased, decreased, and otherwise changed based upon the configuration of recess 2120.

Drape 2304 also includes a top surface 2312 opposite bottom surface 2306. After drape 2304 is placed over cutting template 2100 and dressing 2302, drape 2304 is cut by an edge of a cutting tool. The cutting tool may be, for example, a scalpel, scissors (e.g., safety scissors, etc.), a blade, and other similar implements. The edge of the cutting tool may be pressed on top surface 2312 opposite first gap 2308, such that the edge may cut drape 2304 without interfacing with cutting template 2100 or dressing 2302. As drape 2304 is cut, the edge of the cutting tool may be positioned between first annular surface 2108 and the second annular surface 2112, and may be positioned adjacent first lip surface 2110. In this way, drape 2304 may be cut without cutting dressing 2302, thereby avoiding dislodging of particles therefrom, and without marring or otherwise damaging cutting template 2100, thereby facilitating repeated usage of cutting template 2100 (e.g., with a different drape, etc.). Second gap 2310 may minimize adherence of drape 2304 to cutting template 2100, thereby facilitating more desirable cutting of drape 2304.

In some embodiments, first annular surface 2108, first lip surface 2110, and second annular surface 2112 are configured such that recess 2120 is configured to receive an edge of a target cutting tool. For example, cutting template 2100 may be specifically configured to receive an edge of a scalpel.

As the cutting tool cuts drape 2304, an aperture is formed in drape 2304 and a cutout is separated from drape 2304. After the aperture is formed, a plug of dressing 2302 may protrude through (e.g., stick out from, etc.) the aperture. The cutout may be separated from cutting template 2100 and discarded. A manifold, such as manifold 108, is then adhered to drape 2304 over the aperture. For example, the manifold may include a circular bead of adhesive which is applied to drape 2304 proximate a perimeter of the aperture.

In an exemplary embodiment, bottom surface 2118 is defined by a first surface roughness and top surface 2102 is defined by a second surface roughness less than the first surface roughness. The first surface roughness of bottom surface 2118 may be selected such that movement of cutting template 2100 relative to dressing 2302 is resisted. The surface roughness of bottom surface 2118 may be related to a static frictional coefficient with dressing 2302. For example, the static frictional coefficient of bottom surface 2118 with dressing 2302 may be less than 0.5. Similarly, the surface roughness of top surface 2102 may be related to a static frictional coefficient with drape 2304. For example, the static frictional coefficient of top surface 2102 with drape 2304 may be greater than 0.5.

Eighth Example Cutting Template for use with a NPWT System

Figure 24:
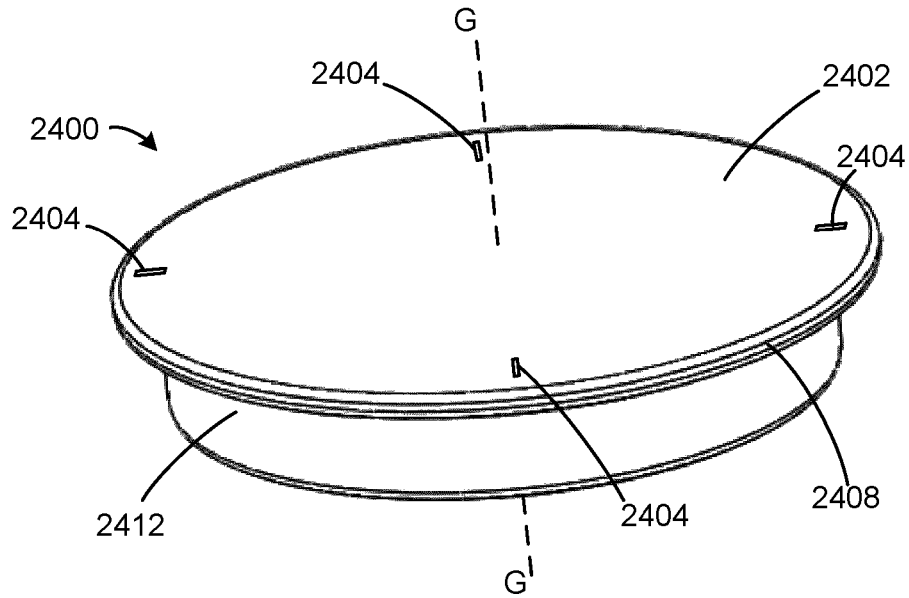
FIG. 24 is a top perspective view of a cutting template for use with a NPWT device, according to an exemplary embodiment.
Figure 25:
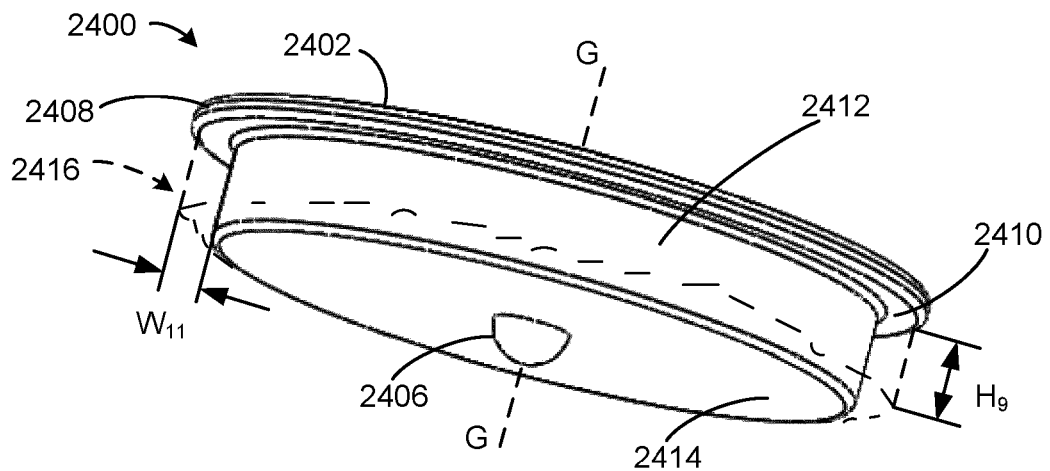
FIG. 25 is a bottom perspective view of the cutting template of FIG. 24, according to an exemplary embodiment.
Figure 26:
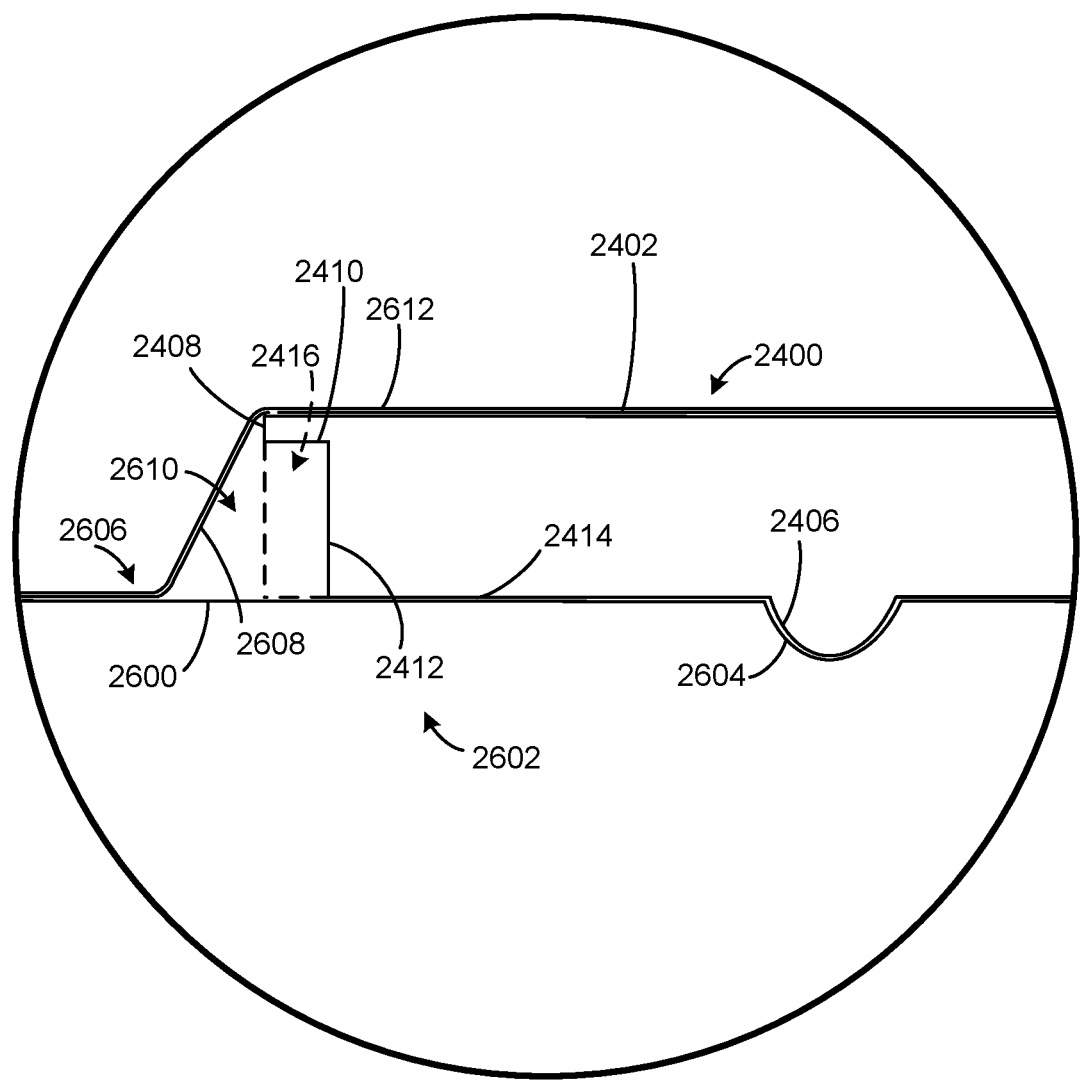
FIG. 26 is a cross-sectional view of a portion of the cutting template of FIG. 24, placed on a dressing and covered with a drape, according to an exemplary embodiment.

Referring now to FIGS. 24-26, a cutting template 2400 is shown, according to an exemplary embodiment. Cutting template 2400 is generally fastener shaped (e.g., mushroom shaped, top hat shaped, plug shaped, etc.) and is generally constructed from portions of two concentric cylinders of different diameters. Cutting template 2400 is centered on a central axis G-G. In various embodiments, cutting template 2400 is rotationally symmetrical about the central axis G-G.

Cutting template 2400 includes a top surface 2402 which is configured to interface with a drape, such as drape 300. In various embodiments, top surface 2402 includes a plurality of graduation marks 2404. Each graduation mark 2404 corresponds with an angular location relative to the central axis G-G. Cutting template 2400 does not include a hole, such as the hole 606. Instead, cutting template 2400 includes a dimple 2406 (e.g., projection, protrusion, protuberance, etc.). As will be explained in more detail herein, dimple 2406 is configured to be received within a depression in a dressing to collocate cutting template 2400 and the dressing.

Top surface 2402 is contiguous with a first annular surface 2408. A border between top surface 2402 and first annular surface 2408 may be beveled, chamfered, rounded, filleted, or otherwise similarly shaped. First annular surface 2408 is defined by a circumference. Graduation marks 2404 correspond with locations along the circumference of first annular surface 2408. For example, one graduation mark 2404 may correspond with a starting point, a second graduation mark 2404 may correspond with 25% of the circumference of first annular surface 2408, a third graduation mark 2404 may correspond with 50% of the circumference of first annular surface 2408, and a fourth graduation mark 2404 may correspond with 75% of the circumference of first annular surface 2408. Prior to covering cutting template 2400 with a drape, cutting template 2400 may be rolled along first annular surface 2408 to measure a length along a dressing or a patient's skin using graduation marks 2404. To facilitate rolling of cutting template 2400, a user's fingers can pinch cutting template 2400 (e.g., with one finger on top surface 2402 and one finger on a bottom surface of cutting template 2400, etc.). In one example, cutting template 2400 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 2404 provides cutting template 2400 with an additional functionality separate from facilitating cutting of a drape. Dimple 2406 may assist a user in locating a center point of cutting template 2400 such that the user may rotate cutting template 2400 about central axis G-G.

First annular surface 2408 is contiguous with a lip surface 2410. A border between first annular surface 2408 and lip surface 2410 may be beveled, chamfered, rounded, filleted, or otherwise similarly shaped. Lip surface 2410 is contiguous with a second annular surface 2412. A border between lip surface 2410 and second annular surface 2412 may be beveled, chamfered, rounded, filleted, or otherwise similarly shaped. Like first annular surface 2408, second annular surface 2412 is centered on the central axis G-G. Second annular surface 2412 is contiguous with a bottom surface 2414. A border between second annular surface 2412 and bottom surface 2414 may be beveled, chamfered, rounded, filleted, or otherwise similarly shaped. Top surface 2402 is substantially disposed along a first plane, lip surface 2410 is substantially disposed along a second plane substantially parallel to the first plane, and bottom surface 2414 is substantially disposed along a third plane substantially parallel to the first plane.

A recess 2416 is formed between a first boundary defined by first annular surface 2408, a second boundary defined by lip surface 2410, a third boundary defined by second annular surface 2412, and a fourth boundary defined by bottom surface 2414. First annular surface 2408 is defined by a thirteenth radius $R_{13}$ and second annular surface 2412 is defined by a fourteenth radius $R_{14}$. A difference between thirteenth radius $R_{13}$ and fourteenth radius $R_{14}$ is equal to an eleventh width $W_{11}$ of lip surface 2410. Various values for thirteenth radius $R_{13}$ and fourteenth radius $R_{14}$ can be selected such that eleventh width $W_{11}$ of lip surface 2410 can be changed, thereby facilitating changing of recess 2416. Additionally, second annular surface 2412 is defined by a ninth height $H_9$ between lip surface 2410 and bottom surface 2414. In an exemplary embodiment, ninth height $H_9$ is 8 mm. In another embodiment, ninth height $H_9$ is 6 mm. A distance between top surface 2402 and lip surface 2410 may be configured such that a distance from bottom surface 2414 to top surface 2402 is between 2 mm and 10 mm, inclusive.

When using cutting template 2400 with an NWPT system, cutting template 2400 is placed on a top surface 2600 of a dressing 2602, which is covering a patient's skin. Dressing 2602 includes a depression 2604. In some applications, depression 2604 is pre-formed (e.g., from a manufacturer of dressing 2602, etc.) in dressing 2602. In other applications, depression 2604 is formed by a user (e.g., using an implement, etc.). Depression 2604 is located at a target location on dressing 2602 so as to facilitate location of a manifold, such as manifold 108, on dressing 2602 at the target location. Depression 2604 and dimple 2406 are configured to collocate cutting template 2400 on dressing 2602. In various embodiments, dimple 2406 is sized and configured to be received in depression 2604. In some embodiments, depression 2604 is sized and configured to receive dimple 2406.

After dimple 2406 has been received in depression 2604, drape 2606 is placed over cutting template 2400 and dressing 2602. Drape 2606 includes a bottom surface 2608 which interfaces with top surface 2402 and top surface 2600, and may at least partially interface with first annular surface 2408. However, cutting template 2400 is configured such that drape 2606 does not substantially interface with lip surface 2410 or second annular surface 2412. Accordingly, a gap 2610 exists between at least lip surface 2410, second annular surface 2412, top surface 2600, and bottom surface 2608. Gap 2610 may also exist between bottom surface 2608 and at least a portion of first annular surface 2408. Gap 2610 may be increased, decreased, and otherwise changed based upon the configuration of recess 2416. For example, gap 2610 is increased if eleventh width $W_{11}$ of lip surface 2410 is increased.

Drape 2606 also includes a top surface 2612 opposite bottom surface 2608. After drape 2606 is placed over cutting template 2400 and dressing 2602, drape 2606 is cut by an edge of a cutting tool. The cutting tool may be, for example, a scalpel, scissors (e.g., safety scissors, etc.), a blade, and other similar implements. The edge of the cutting tool may be pressed on top surface 2612 opposite gap 2610, such that the edge may cut drape 2606 without interfacing with cutting template 2400 or dressing 2602. In this way, drape 2606 may be cut without cutting dressing 2602, thereby avoiding dislodging of particles therefrom, and without marring or otherwise damaging cutting template 2400, thereby facilitating repeated usage of cutting template 2400 (e.g., with a different drape, etc.).

As the cutting tool cuts drape 2606, an aperture is formed in drape 2606 and a cutout is separated from drape 2606. After the aperture is formed, a plug of dressing 2602 may protrude through (e.g., stick out from, etc.) the aperture. The cutout may be separated from cutting template 2400 and discarded. A manifold, such as manifold 108, is then adhered to drape 2606 over the aperture. For example, the manifold may include a circular bead of adhesive which is applied to drape 2606 proximate a perimeter of the aperture.

In an exemplary embodiment, bottom surface 2414 is defined by a first surface roughness and top surface 2402 is defined by a second surface roughness less than the first surface roughness. The first surface roughness of bottom surface 2414 may be selected such that movement of cutting template 2400 relative to dressing 2602 is resisted. The surface roughness of bottom surface 2414 may be related to a static frictional coefficient with dressing 2602. For example, the static frictional coefficient of bottom surface 2414 with dressing 2602 may be less than 0.5. Similarly, the surface roughness of top surface 2402 may be related to a static frictional coefficient with drape 2606. For example, the static frictional coefficient of top surface 2402 with drape 2606 may be greater than 0.5.

Ninth Example Cutting Template for Use with a NPWT System

Figure 27:
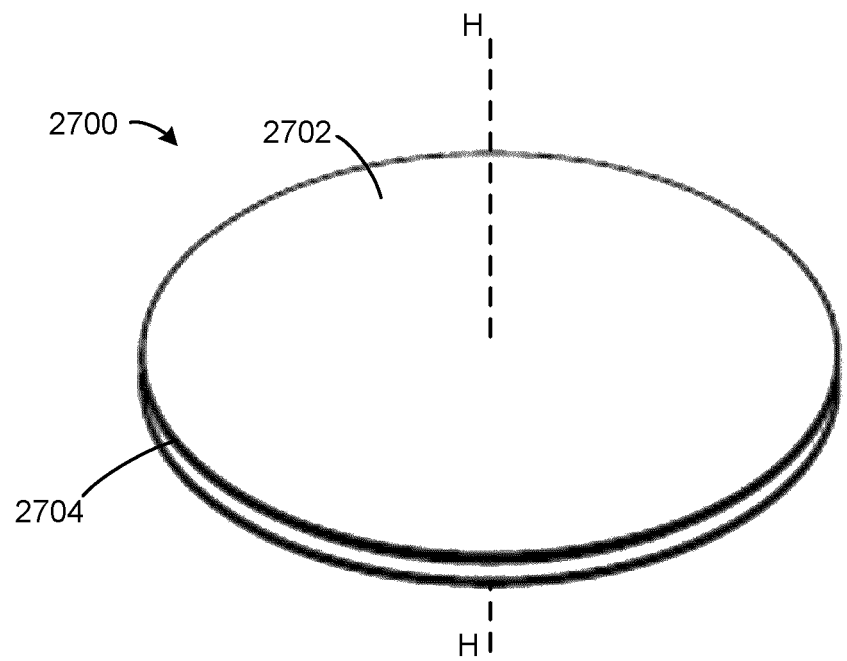
FIG. 27 is a top perspective view of a cutting template for use with a NPWT device, according to an exemplary embodiment.
Figure 28:
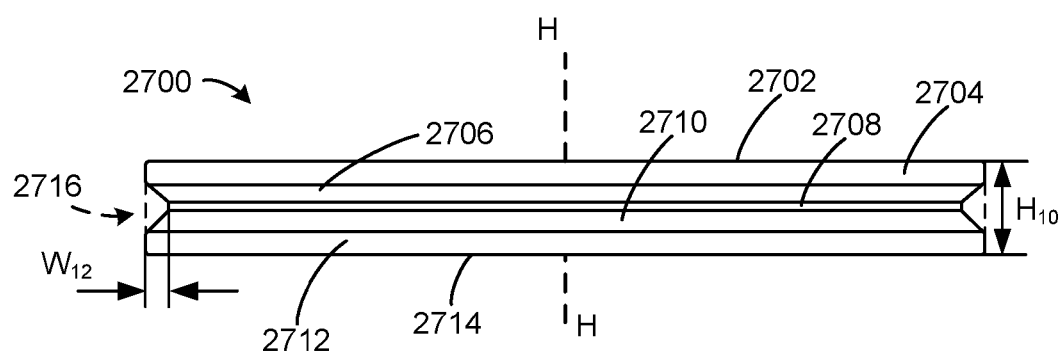
FIG. 28 is a bottom perspective view of the cutting template of FIG. 27, according to an exemplary embodiment.
Figure 29:
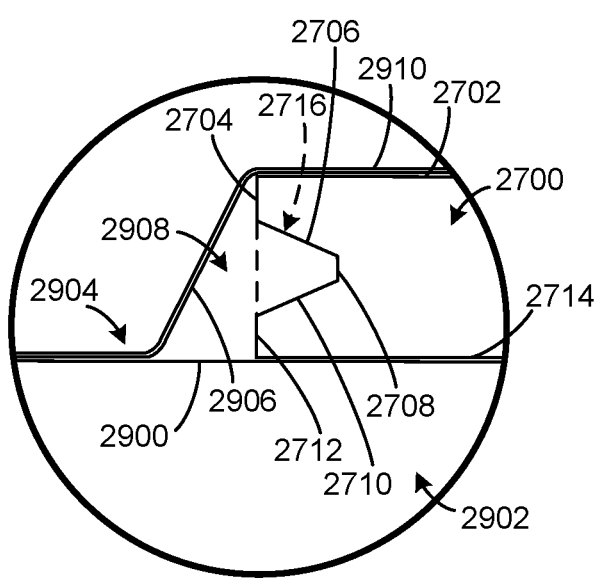
FIG. 29 is a cross-sectional view of a portion of the cutting template of FIG. 27, placed on a dressing and covered with a drape, according to an exemplary embodiment.

Referring now to FIGS. 27-29, a cutting template 2700 is shown, according to an exemplary embodiment. Cutting template 2700 is generally hourglass shaped and is generally constructed from portions of two concentric cylinders of different diameters. Cutting template 2700 is centered on a central axis H-H. In various embodiments, cutting template 2700 is rotationally symmetrical about the central axis H-H.

Cutting template 2700 includes a top surface 2702 which is configured to interface with a drape, such as drape 300. In various embodiments, top surface 2702 includes a plurality of graduation marks, such as graduation marks 604, a hole, such as hole 606, or a dimple, such as dimple 2406. Top surface 2702 is contiguous with a first annular surface 2704. A border between top surface 2702 and first annular surface 2704 may be beveled, chamfered, rounded, filleted, or otherwise similarly shaped.

First annular surface 2704 is contiguous with a first lip surface 2706. A border between first annular surface 2704 and first lip surface 2706 may be beveled, chamfered, rounded, filleted, or otherwise similarly shaped. First lip surface 2706 is contiguous with a second annular surface 2708. A border between first lip surface 2706 and second annular surface 2708 may be beveled, chamfered, rounded, filleted, or otherwise similarly shaped. Second annular surface 2708 is contiguous with a second lip surface 2710. A border between second annular surface 2708 and second lip surface 2710 may be beveled, chamfered, rounded, filleted, or otherwise similarly shaped. Second lip surface 2710 is contiguous with a third annular surface 2712. A border between second lip surface 2710 and third annular surface 2712 may be beveled, chamfered, rounded, filleted, or otherwise similarly shaped. Third annular surface 2712 is contiguous with a bottom surface 2714. A border between third annular surface 2712 and bottom surface 2714 may be beveled, chamfered, rounded, filleted, or otherwise similarly shaped. First annular surface 2704, second annular surface 2708, and third annular surface 2712 are centered on the central axis H-H. Top surface 2702 is substantially disposed along a first plane and bottom surface 2714 is substantially disposed along a second plane substantially parallel to the first plane.

A recess 2716 is formed between a first boundary defined by first annular surface 2704, a second boundary defined by first lip surface 2706, a third boundary defined by second annular surface 2708, a fourth boundary defined by second lip surface 2710, and a fifth boundary defined by third annular surface 2712. First annular surface 2704 is defined by a fifteenth radius $R_{15}$ and second annular surface 2708 is defined by a sixteenth radius $R_{16}$. In some embodiments, fifteenth radius $R_{15}$ is equal to 4.5 cm and sixteenth radius $R_{16}$ is equal to 4.3 cm. A difference between fifteenth radius $R_{15}$ and sixteenth radius $R_{16}$ is equal to a twelfth width Wit of second annular surface 2708. Various values for fifteenth radius $R_{15}$ and sixteenth radius $R_{16}$ can be selected such that twelfth width $W_{12}$ of second annular surface 2708 can be changed, thereby facilitating changing of recess 2716. Additionally, cutting template 2700 is defined by a tenth height $H_{10}$ between top surface 2702 and bottom surface 2714. In an exemplary embodiment, tenth height $H_{10}$ is 2.5 mm. In another embodiment, tenth height $H_{10}$ is 6 mm. In yet another embodiment, tenth height $H_{10}$ is 8 mm Tenth height $H_{10}$ may be between 2 mm and 10 mm, inclusive. In some embodiments, twelfth width $W_{12}$ is 1 mm.

When using cutting template 2700 with an NWPT system, cutting template 2700 is placed on a top surface 2900 of a dressing 2902, which is covering a patient's skin. Drape 2904 is then placed over cutting template 2700 and dressing 2902. Drape 2904 includes a bottom surface 2906 which interfaces with top surface 2702 and top surface 2900, and may at least partially interface with first annular surface 2704. However, cutting template 2700 is configured such that drape 2904 does not substantially interface with first lip surface 2706, second annular surface 2708, or second lip surface 2710. Accordingly, a gap 2908 exists between at least first lip surface 2706, second annular surface 2708, second lip surface 2710, top surface 2900, bottom surface 2906, and third annular surface 2712. Gap 2908 may also exist between bottom surface 2906 and at least a portion of first annular surface 2704. Gap 2908 may be increased, decreased, and otherwise changed based upon the configuration of recess 2716. For example, gap 2908 is increased if the twelfth width $W_{12}$ is increased.

Drape 2904 also includes a top surface 2910 opposite bottom surface 2906. After drape 2904 is placed over cutting template 2700 and dressing 2902, drape 2904 is cut by an edge of a cutting tool. The cutting tool may be, for example, a scalpel, scissors (e.g., safety scissors, etc.), a blade, and other similar implements. The edge of the cutting tool may be pressed on top surface 2910 opposite gap 2908, such that the edge may cut drape 2904 without interfacing with cutting template 2700 or dressing 2902. In this way, drape 2904 may be cut without cutting dressing 2902, thereby avoiding dislodging of particles therefrom, and without marring or otherwise damaging cutting template 2700, thereby facilitating repeated usage of cutting template 2700 (e.g., with a different drape, etc.).

As the cutting tool cuts drape 2904, an aperture is formed in drape 2904 and a cutout is separated from drape 2904. After the aperture is formed, a plug of dressing 2902 may protrude through (e.g., stick out from, etc.) the aperture. The cutout may be separated from cutting template 2700 and discarded. A manifold, such as manifold 108, is then adhered to drape 2904 over the aperture. For example, the manifold may include a circular bead of adhesive which is applied to drape 2904 proximate a perimeter of the aperture.

In an exemplary embodiment, bottom surface 2714 is defined by a first surface roughness and top surface 2702 is defined by a second surface roughness less than the first surface roughness. The first surface roughness of bottom surface 2714 may be selected such that movement of cutting template 2700 relative to dressing 2902 is resisted. The surface roughness of bottom surface 2714 may be related to a static frictional coefficient with dressing 2902. For example, the static frictional coefficient of bottom surface 2714 with dressing 2902 may be less than 0.5. Similarly, the surface roughness of top surface 2702 may be related to a static frictional coefficient with drape 2904. For example, the static frictional coefficient of top surface 2702 with drape 2904 may be greater than 0.5.

Tenth Example Cutting Template for Use with a NPWT System

Figure 30:
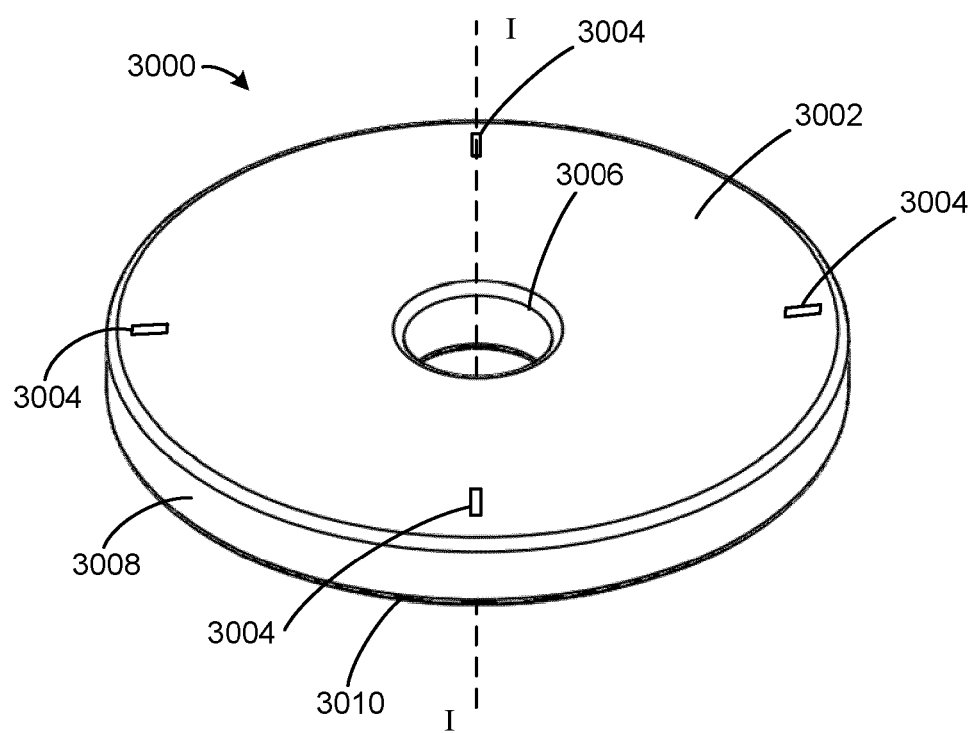
FIG. 30 is a top perspective view of a cutting template for use with a NPWT device, according to an exemplary embodiment.

Referring now to FIG. 30, a cutting template 3000 is shown, according to an exemplary embodiment. Cutting template 3000 is generally cylindrical. Cutting template 3000 is centered on a central axis I-I. In various embodiments, cutting template 3000 is rotationally symmetrical about the central axis I-I.

Cutting template 3000 includes a top surface 3002 which is configured to interface with a drape, such as drape 300. In various embodiments, top surface 3002 includes a plurality of graduation marks 3004. Each graduation mark 3004 corresponds with an angular location relative to the central axis I-I. Cutting template 3000 also includes a hole 3006 centered on the central axis I-I and extending through cutting template 3000.

Top surface 3002 is contiguous with an annular surface 3008. A border between top surface 3002 and annular surface 3008 may be beveled, chamfered, rounded, filleted, or otherwise similarly shaped. Annular surface 3008 is defined by a circumference. Graduation marks 3004 correspond with locations along the circumference of annular surface 3008. For example, one graduation mark 3004 may correspond with a starting point, a second graduation mark 3004 may correspond with 25% of the circumference of annular surface 3008, a third graduation mark 3004 may correspond with 50% of the circumference of annular surface 3008, and a fourth graduation mark 3004 may correspond with 75% of the circumference of annular surface 3008. Prior to covering cutting template 3000 with a drape, cutting template 3000 may be rolled along annular surface 3008 to measure a length along a dressing or a patient's skin using graduation marks 3004. To facilitate rolling of cutting template 3000, a user's finger or an implement may be placed through or into hole 3006. In one example, cutting template 3000 may be rolled along a patient's skin around a tissue wound to determine a length and/or a width of the tissue wound. Measuring the length and/or width of the tissue wound may be frequently performed (e.g., with every change of a dressing, etc.). In this way, graduation marks 3004 and hole 3006 provide cutting template 3000 with an additional functionality separate from facilitating cutting of a drape.

Annular surface 3008 is contiguous with a bottom surface 3010. A border between annular surface 3008 and bottom surface 3010 may be beveled, chamfered, rounded, filleted, or otherwise similarly shaped. Top surface 3002 is substantially disposed along a first plane and bottom surface 3010 is substantially disposed along a second plane substantially parallel to the first plane.

Annular surface 3008 is defined by a seventeenth radius $R_{17}$. In some embodiments, the seventeenth radius $R_{17}$ is approximately 3.5 cm. Hole 3006 is defined by an eighteenth radius $R_{18}$. In some embodiments, the eighteenth radius $R_{18}$ is approximately 3 mm Additionally, annular surface 3008 is defined by an eleventh $H_{11}$ between top surface 3002 and bottom surface 3010. In an exemplary embodiment, eleventh height $H_{11}$ is 3 mm.

When using cutting template 3000 with an NWPT system, cutting template 3000 is placed on a top surface of a dressing, which is covering a patient's skin. Next, a drape is placed over cutting template 3000 and the dressing. The drape includes a bottom surface which interfaces with top surface 3002 and the top surface of the dressing, and may at least partially interface with annular surface 3008. Accordingly, a gap exists between at least a portion of annular surface 3008, the top surface of the dressing, and the bottom surface of the drape. The gap may be increased, decreased, and otherwise changed based upon the configuration of annular surface 3008.

The drape also includes a top surface opposite the bottom surface of the drape. After the drape is placed over cutting template 3000 and the dressing, the drape is cut by an edge of a cutting tool. The cutting tool may be, for example, a scalpel, scissors (e.g., safety scissors, etc.), a blade, and other similar implements. The edge of the cutting tool may be pressed on the top surface of the drape opposite the gap, such that the edge may cut the drape without interfacing with cutting template 3000 or the dressing. In this way, the drape may be cut without cutting the dressing, thereby avoiding dislodging of particles therefrom, and without marring or otherwise damaging cutting template 3000, thereby facilitating repeated usage of cutting template 3000 (e.g., with a different drape, etc.).

As the cutting tool cuts the drape, an aperture is formed in the drape and a cutout is separated from the drape. After the aperture is formed, a plug of the dressing may protrude through (e.g., stick out from, etc.) the aperture. The cutout may be separated from cutting template 3000 and discarded. A manifold, such as manifold 108, is then adhered to the drape over the aperture. For example, the manifold may include a circular bead of adhesive which is applied to the drape proximate a perimeter of the aperture.

In an exemplary embodiment, bottom surface 3010 is defined by a first surface roughness and top surface 3002 is defined by a second surface roughness less than the first surface roughness. The first surface roughness of bottom surface 3010 may be selected such that movement of cutting template 3000 relative to the dressing is resisted. The surface roughness of bottom surface 3010 may be related to a static frictional coefficient with the dressing. For example, the static frictional coefficient of bottom surface 3010 with the dressing may be less than 0.5. Similarly, the surface roughness of top surface 3002 may be related to a static frictional coefficient with the drape. For example, the static frictional coefficient of top surface 3002 with the drape may be greater than 0 5

Kit for Use with a NPWT Device

Figure 31:
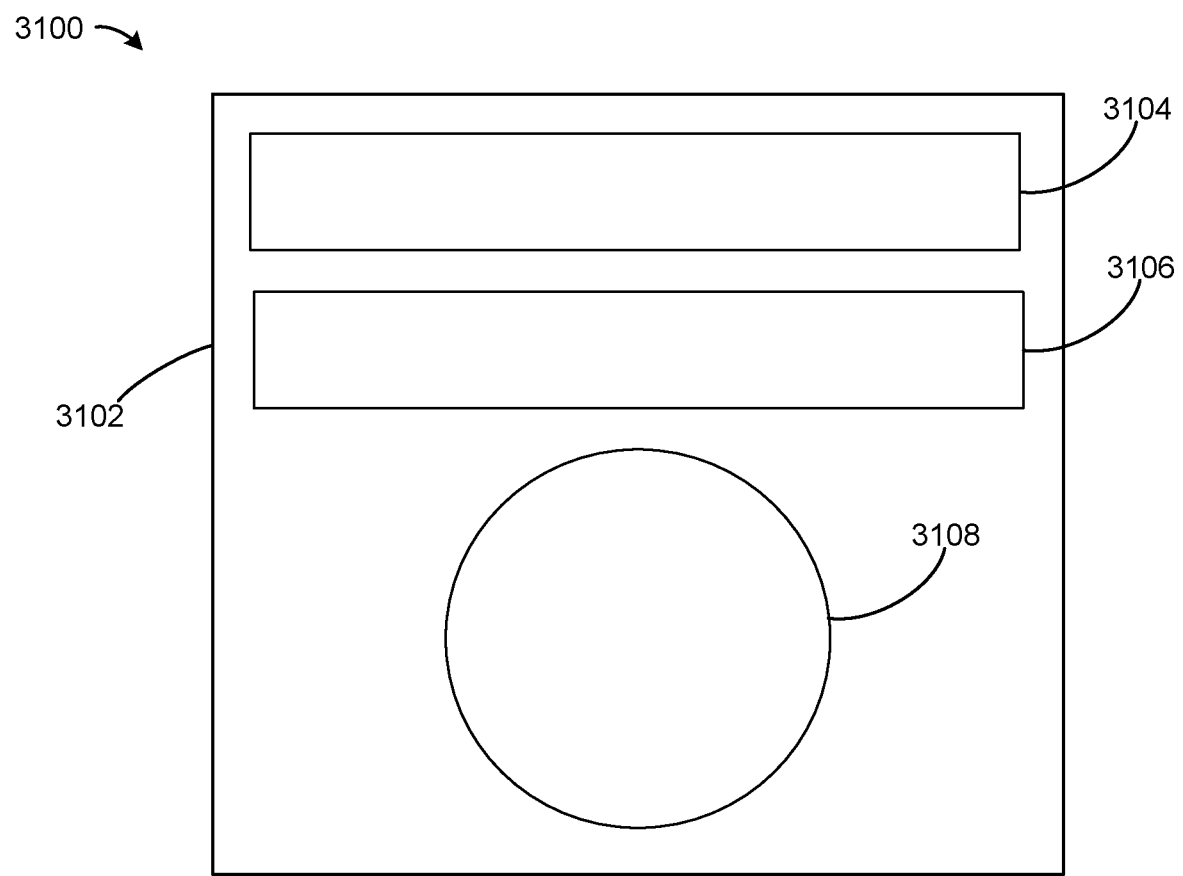
FIG. 31 is a drawing of a kit for use with a NPWT device, according to an exemplary embodiment.

Referring now to FIG. 31, a kit 3100 is shown, according to an exemplary embodiment. Kit 3100 is for use with a NPWT device, such as therapy device 102. Kit 3100 includes a package 3102. Package 3102 defines a sterilized interior environment. Package 3102 may be a bag, a case, and other similar structures. Kit 3100 also includes a dressing layer 3104. Dressing layer 3104 is disposed within package 3102. Dressing layer 3104 may be any of dressing 110, dressing 202, dressing 802, dressing 1002, dressing 1302, dressing 1702, dressing 2002, dressing 2302, dressing 2602, and dressing 2902, alone or in combination. Kit 3100 also includes a drape layer 3106. Drape layer 3106 is disposed within package 3102. Drape layer 3106 may be any of drape 300, drape 804, drape 1004, drape 1304, drape 1704, drape 2004, drape 2304, drape 2606, and drape 2904, alone or in combination. Kit 3100 also includes a cutting template 3108. Cutting template 3108 is disposed within package 3102. Cutting template 3108 may be any of cutting template 200, cutting template 600, cutting template 900, cutting template 1200, cutting template 1500, cutting template 1800, cutting template 2100, cutting template 2400, cutting template 2700, and cutting template 3000, alone or in combination.

Method of Cutting a Drape for Use with a NPWT Device

Figure 32:
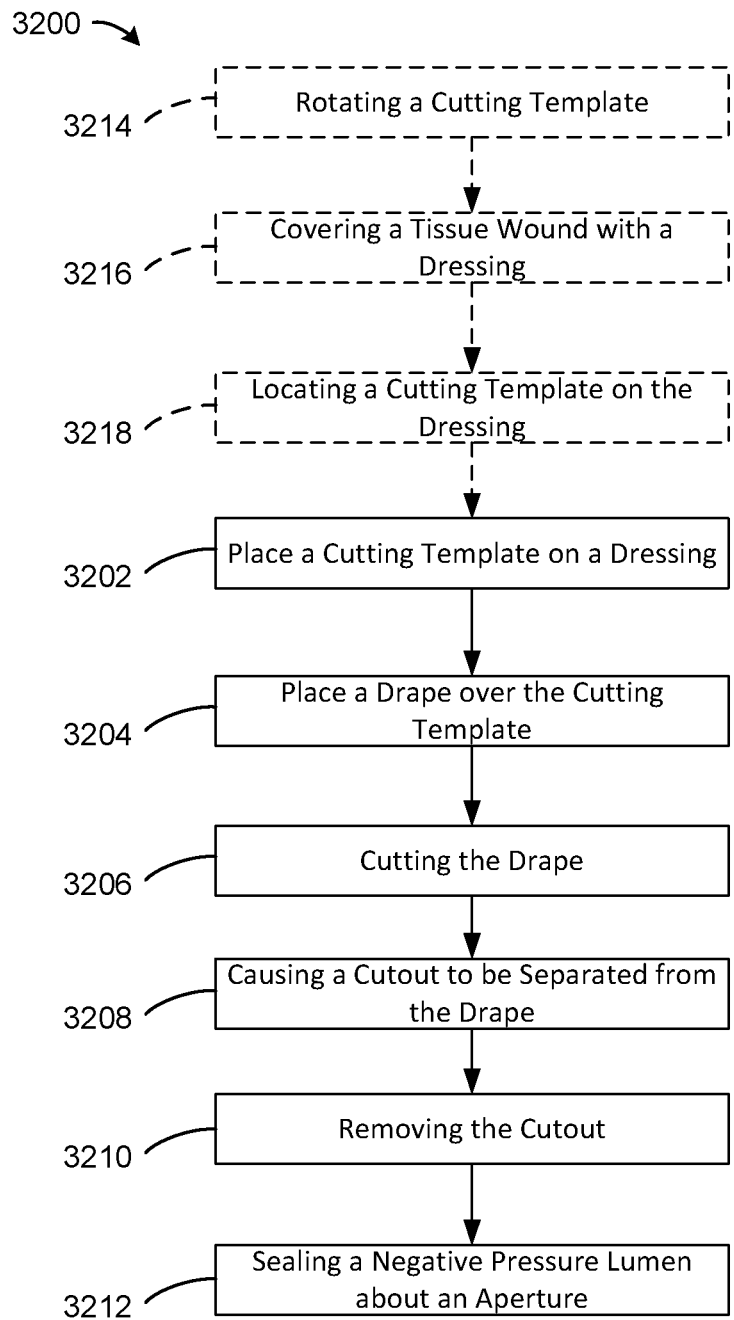
FIG. 32 is a block diagram of a method of cutting a drape for use with a NPWT device, according to an exemplary embodiment.

Referring now to FIG. 32, a method of cutting a drape for use with a NPWT device 3200 is shown, according to an exemplary embodiment. Method 3200 may be implemented with a NPWT device, such as therapy device 102. Method 3200 is implemented with a cutting template, a dressing, and a drape. The cutting template may be any of cutting template 200, cutting template 600, cutting template 900, cutting template 1200, cutting template 1500, cutting template 1800, cutting template 2100, cutting template 2400, and cutting template 2700, alone or in combination. The dressing may be any of dressing 110, dressing 202, dressing 802, dressing 1002, dressing 1302, dressing 1702, dressing 2002, dressing 2302, dressing 2602, and dressing 2902, alone or in combination. The drape may be any of drape 300, drape 804, drape 1004, drape 1304, drape 1704, drape 2004, drape 2304, drape 2606, and drape 2904, alone or in combination.

Method 3200 includes, in block 3202, placing a cutting template on a dressing. Method 3200 then includes, in block 3204, placing a drape over the cutting template. The drape may be placed over the cutting template such that the drape covers the cutting template and the dressing. The drape may only cover part of the dressing. Method 3200 then includes, in block 3206, cutting the drape. The drape may be cut by pressing an implement against the drape such that the implement presses the drape towards the cutting template, thereby causing the drape to be cut. Method 3200 then includes, in block 3208, causing a cutout to be separated from the drape. The cutout may be separated from the drape by rotating the implement about the cutting template, thereby causing the cutout to be separated from the drape and an aperture to be simultaneously formed in the drape. Method 3200 then includes, in block 3210, removing the cutout. The cutout may be removed from the aperture. Method 3200 then includes, in block 3212, sealing a negative pressure lumen of the NPWT device about the aperture.

Method 3200 may also include, prior to placing the cutting template on the dressing, in block 3214, rotating the cutting template. The cutting tool may be rotated along a perimeter of a wound bed or tissue wound. Method 3200 may also include, prior to placing the cutting template on the dressing, in block 3216, covering a tissue would with the dressing. The dressing may be placed over at least a portion of the wound bed or tissue wound. Method 3200 may also include, prior to placing the cutting template on the dressing, in block 3218, locating the cutting template on the dressing. A dimple on the cutting template may be received in a divot on the dressing.

Configurations of Cutting Template for Use with a NPWT System

The various features of cutting template 200, cutting template 600, cutting template 900, cutting template 1200, cutting template 1500, cutting template 1800, cutting template 2100, cutting template 2400, and cutting template 2700 described herein are for illustrative purposes only and are not intended be limiting. For example, any features described with relation to any of cutting template 200, cutting template 600, cutting template 900, cutting template 1200, cutting template 1500, cutting template 1800, cutting template 2100, cutting template 2400, and cutting template 2700 may similarly be implemented on any of the others of cutting template 200, cutting template 600, cutting template 900, cutting template 1200, cutting template 1500, cutting template 1800, cutting template 2100, cutting template 2400, and cutting template 2700.

In some embodiments, top surface 208, top surface 602, top surface 902, top surface 1202, top surface 1502, top surface 1802, top surface 2102, top surface 2402, top surface 2702, and/or top surface 3002 include an annular ring or rim along which an edge of a cutting tool can be drawn to cut a drape. This annular ring or rim may provide an additional functionality to cutting template 200, cutting template 600, cutting template 900, cutting template 1200, cutting template 1500, cutting template 1800, cutting template 2100, cutting template 2400, and/or cutting template 2700.

In some embodiments, hole 606, hole 906, hole 1206, hole 1506, hole 1806, hole 2106, and/or hole 3006 is an indentation rather than a hole (e.g., does not extend entirely from a top surface to a bottom surface, etc.). For example, hole 3006 may be an indentation in top surface 3002 that does not extend to bottom surface 3010. In some embodiments, hole 606, hole 906, hole 1206, hole 1506, hole 1806, hole 2106, and/or hole 3006 has a diameter of 7 mm.

The surface roughness of bottom surface 204, bottom surface 614, bottom surface 914, bottom surface 1214, bottom surface 1518, bottom surface 1818, bottom surface 2118, bottom surface 2414, bottom surface 2714, and bottom surface 3010 may be approximately equivalent to a surface roughness of a relatively high grit sandpaper (e.g., 220 grit, etc.). Additionally or alternatively, bottom surface 204, bottom surface 614, bottom surface 914, bottom surface 1214, bottom surface 1518, bottom surface 1818, bottom surface 2118, bottom surface 2414, bottom surface 2714, and bottom surface 3010 may be otherwise textured or coated to minimize movement with a dressing. For example, bottom surface 204, bottom surface 614, bottom surface 914, bottom surface 1214, bottom surface 1518, bottom surface 1818, bottom surface 2118, bottom surface 2414, bottom surface 2714, and bottom surface 3010 may be coated in a non-slip coating.

In various embodiments, cutting template 200, cutting template 600, cutting template 900, cutting template 1200, cutting template 1500, cutting template 1800, cutting template 2100, cutting template 2400, and cutting template 2700 are at least partially transparent or translucent. This transparency and/or translucency may assist a user in locating cutting template 200, cutting template 600, cutting template 900, cutting template 1200, cutting template 1500, cutting template 1800, cutting template 2100, cutting template 2400, cutting template 2700 relative to a tissue wound. In some embodiments, cutting template 200, cutting template 600, cutting template 900, cutting template 1200, cutting template 1500, cutting template 1800, cutting template 2100, cutting template 2400, and cutting template 2700 are at least partially opaque.

In various embodiments, cutting template 200, cutting template 600, cutting template 900, cutting template 1200, cutting template 1500, cutting template 1800, cutting template 2100, cutting template 2400, and/or cutting template 2700 are integrated in (e.g., initially adhered to, initially positioned within, etc.) a dressing. In this way, cutting template 200, cutting template 600, cutting template 900, cutting template 1200, cutting template 1500, cutting template 1800, cutting template 2100, cutting template 2400, and/or cutting template 2700 may be sold along with the dressing, thereby increasing the desirability of the dressing. Additionally, integrating cutting template 200, cutting template 600, cutting template 900, cutting template 1200, cutting template 1500, cutting template 1800, cutting template 2100, cutting template 2400, and/or cutting template 2700 within a dressing ensures that cutting template 200, cutting template 600, cutting template 900, cutting template 1200, cutting template 1500, cutting template 1800, cutting template 2100, cutting template 2400, and/or cutting template 2700 are located in a target position. For example, a dressing for a target tissue wound repair may be sold with cutting template 200 integrated at a target location associated with the target tissue wound repair, thereby facilitating more rapid treatment of the tissue wound (e.g., in triage situations, etc.).

Cutting template 200, cutting template 600, cutting template 900, cutting template 1200, cutting template 1500, cutting template 1800, cutting template 2100, cutting template 2400, and/or cutting template 2700 may be sterilized. For example, cutting template 200, cutting template 600, cutting template 900, cutting template 1200, cutting template 1500, cutting template 1800, cutting template 2100, cutting template 2400, and/or cutting template 2700 may be sold in a sterile container (e.g., without a dressing, integrated within a dressing, etc.).

In various embodiments, top surface 208, top surface 602, top surface 902, top surface 1202, top surface 1502, top surface 1802, top surface 2102, top surface 2402, top surface 2702, and top surface 3002 may be treated with an adhesive resistant coating. This adhesive resistant coating may decrease the ability of a drape to adhere to top surface 208, top surface 602, top surface 902, top surface 1202, top surface 1502, top surface 1802, top surface 2102, top surface 2402, top surface 2702, and/or top surface 3002.

Cutting template 200, cutting template 600, cutting template 900, cutting template 1200, cutting template 1500, cutting template 1800, cutting template 2100, cutting template 2400, and/or cutting template 2700 may be reusable, disposable, and/or recyclable.

Cutting template 200, cutting template 600, cutting template 900, cutting template 1200, cutting template 1500, cutting template 1800, cutting template 2100, cutting template 2400, and/or cutting template 2700 may include a plurality (e.g., twelve, sixty, etc.) of graduation marks. The graduation marks may include major graduation marks (e.g., every fifteen degrees, etc.) and minor graduation marks (e.g., every three degrees, etc.). Furthermore, any of the graduation marks may include a notch or slot (e.g., from a top surface of the cutting template to a bottom surface of the cutting template, etc.) to facilitate cutting of the drape along the notch. In one embodiment, cutting template 200, cutting template 600, cutting template 900, cutting template 1200, cutting template 1500, cutting template 1800, cutting template 2100, cutting template 2400, and/or cutting template 2700 has a top surface with a circumference of 12 cm and includes twelve major graduation marks, each 1 cm apart, with four minor graduation marks equally spaced between each of the major graduation marks.

In some embodiments, cutting template 200, cutting template 600, cutting template 900, cutting template 1200, cutting template 1500, cutting template 1800, cutting template 2100, cutting template 2400, and/or cutting template 2700 includes a marking device for marking a dressing. The marking device may automatically mark, or be used to mark, the dressing as cutting template 200, cutting template 600, cutting template 900, cutting template 1200, cutting template 1500, cutting template 1800, cutting template 2100, cutting template 2400, and/or cutting template 2700 is rolled along the dressing. The marking device may be located on or near a graduation mark. The marking device may be, for example, a grease pen or marker.

In various embodiments, a drape is cut using a customized or adapted cutting tool designed to coordinate with cutting template 200, cutting template 600, cutting template 900, cutting template 1200, cutting template 1500, cutting template 1800, cutting template 2100, cutting template 2400, and/or cutting template 2700 to cut the drape.

Dressing 110, dressing 202, dressing 802, dressing 1002, dressing 1302, dressing 1702, dressing 2002, dressing 2302, dressing 2602, and/or dressing 2902 may be foam and/or may include foam dressing layers.

In some embodiments, cutting template 200, cutting template 600, cutting template 900, cutting template 1200, cutting template 1500, cutting template 1800, cutting template 2100, cutting template 2400, and/or cutting template 2700 include a mechanism for attachment to a keychain, lanyard, carabiner, d-clip, or other similar structure.

In some embodiments, cutting template 200, cutting template 600, cutting template 900, cutting template 1200, cutting template 1500, cutting template 1800, cutting template 2100, cutting template 2400, and/or cutting template 2700 are constructed from a biocompatible material. Cutting template 200, cutting template 600, cutting template 900, cutting template 1200, cutting template 1500, cutting template 1800, cutting template 2100, cutting template 2400, and/or cutting template 2700 may be constructed from, for example, biocompatible polymer, styrene, polystyrene, and other similar materials. Cutting template 200, cutting template 600, cutting template 900, cutting template 1200, cutting template 1500, cutting template 1800, cutting template 2100, cutting template 2400, and/or cutting template 2700 may be substantially hard and rigid (e.g., compared to a dressing, etc.). For example, cutting template 200, cutting template 600, cutting template 900, cutting template 1200, cutting template 1500, cutting template 1800, cutting template 2100, cutting template 2400, and/or cutting template 2700 may be substantially rigid so as to withstand numerous uses thereof (e.g., numerous interactions with an edge of a cutting tool, etc.). Additionally, the substantially rigid nature of cutting template 200, cutting template 600, cutting template 900, cutting template 1200, cutting template 1500, cutting template 1800, cutting template 2100, cutting template 2400, and/or cutting template 2700 facilitates accurate and repeatable cutting of a drape (e.g., each aperture produced is approximately the same, etc.). In various embodiments, cutting template 200, cutting template 600, cutting template 900, cutting template 1200, cutting template 1500, cutting template 1800, cutting template 2100, cutting template 2400, and/or cutting template 2700 has a Brinell hardness number of at least 15 (e.g., 15, 17, 20, 25, etc.).

In some embodiments, cutting template 200, cutting template 600, cutting template 900, cutting template 1200, cutting template 1500, cutting template 1800, cutting template 2100, cutting template 2400, and/or cutting template 2700 include a hole and at least one dimple. For example cutting template 200, cutting template 600, cutting template 900, cutting template 1200, cutting template 1500, cutting template 1800, cutting template 2100, cutting template 2400, and/or cutting template 2700 may include a hole along a central axis thereof and a plurality of dimples disposed around the hole.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A cutting template for use with a negative pressure wound therapy system, the cutting template comprising:
a substantially rigid body, the body comprising:
a top surface configured to engage a drape layer;
a bottom surface configured to engage a dressing layer;
a height defined between the top surface and the bottom surface, the height configured to create a gap between the drape layer and the dressing layer;
a first annular surface disposed between the top surface and the bottom surface; and
a second annular surface contiguous with the top surface and extending towards the bottom surface; and
a recess disposed substantially about a perimeter of the body;
wherein the recess is configured to receive an edge of a cutting tool so that an opening is formed in the drape layer when the edge is traversed about the perimeter, and wherein at least part of the recess is formed between the first annular surface and the second annular surface.

2. The cutting template of claim 1, wherein the bottom surface comprises a dimple protruding from the bottom surface.

3. The cutting template of claim 1, wherein the top surface comprises a plurality of graduation marks, each of the plurality of graduation marks corresponding with a circumferential location about the top surface.

4. The cutting template of claim 1, further comprising a hole centered on a center point of the top surface and extending from the top surface through the body to the bottom surface.

5. The cutting template of claim 1, wherein the bottom surface is at least one of textured and coated with a non-slip coating.

6. A cutting template for use with a negative pressure wound therapy system, the cutting template comprising:
a top surface configured to interface with a drape;
a bottom surface configured to interface with a dressing;
a first annular surface contiguous with the bottom surface and extending orthogonally from the bottom surface towards the top surface, the first annular surface defined by a first diameter;
a second annular surface contiguous with the top surface and extending orthogonally from the top surface towards the bottom surface, the second annular surface defined by a second diameter different from the first diameter; and
a lip surface contiguous with the first annular surface and the second annular surface.

7. The cutting template of claim 6, wherein:
the top surface is substantially disposed along a first plane; and
the lip surface is substantially disposed along a second plane substantially parallel to the first plane.

8. The cutting template of claim 7, wherein:
the bottom surface is substantially disposed along a third plane; and
a first distance between the first plane and the second plane is less than a second distance between the third plane and the second plane.

9. The cutting template of claim 6, wherein:
the top surface has a first surface roughness; and
the bottom surface has a second surface roughness greater than the first surface roughness.

10. The cutting template of claim 6, wherein the cutting template is constructed from a biocompatible polymer.

11. A cutting template for use with a negative pressure wound therapy system, the cutting template comprising:
a substantially rigid body, the body comprising:
a top surface configured to engage a drape layer;
a bottom surface configured to engage a dressing layer;
a height defined between the top surface and the bottom surface, the height configured to create a gap between the drape layer and the dressing layer;
a first annular surface disposed between the top surface and the bottom surface; and
a second annular surface disposed between the top surface and the bottom surface; and
a recess disposed substantially about a perimeter of the body;
wherein the recess is configured to receive an edge of a cutting tool so that an opening is formed in the drape layer when the edge is traversed about the perimeter, and wherein at least part of the recess is formed between the first annular surface and the second annular surface.

12. A cutting template for use with a negative pressure wound therapy system, the cutting template comprising:
a substantially rigid body, the body comprising:
 a top surface configured to engage a drape layer;
 a bottom surface configured to engage a dressing layer;
 a height defined between the top surface and the bottom surface, the height configured to create a gap between the drape layer and the dressing layer;
 a first annular surface contiguous with the bottom surface and extending orthogonally from the bottom surface towards the top surface, the first annular surface defined by a first diameter; and
 a second annular surface contiguous with the top surface and extending orthogonally from the top surface towards the bottom surface, the second annular surface defined by a second diameter different from the first diameter; and
 a recess disposed substantially about a perimeter of the body;
 wherein the recess is configured to receive an edge of a cutting tool so that an opening is formed in the drape layer when the edge is traversed about the perimeter, wherein one of the first annular surface and the second annular surface is inset relative to the other of the first annular surface and the second annular surface to form the recess.

13. A kit for use with a negative pressure wound therapy device, the kit comprising:
 a package defining a sterilized interior environment;
 a dressing layer disposed within the sterilized interior environment;
 a drape layer disposed within the sterilized interior environment; and
 a cutting template disposed within the sterilized interior environment;
 wherein the cutting template comprises a top surface, a bottom surface, and a recess disposed about a perimeter of the cutting template, the recess configured to receive an edge of a cutting tool, and wherein:
  the top surface is configured to interface with the drape layer,
  the bottom surface is configured to interface with the dressing layer, and
  the cutting template further comprises a first annular surface contiguous with the bottom surface and extending orthogonally from the bottom surface towards the top surface, and a second annular surface contiguous with the top surface and extending orthogonally from the top surface towards the bottom surface.

14. The kit of claim 13, wherein the drape layer is configured to be cut by the cutting tool when the edge engages the recess and is traversed about the perimeter.

15. The kit of Claim 13, wherein:
 the cutting template comprises a lip surface contiguous with the first annular surface and the second annular surface;
 the top surface is substantially disposed along a first plane; and
 the lip surface is substantially disposed along a second plane substantially parallel to the first plane.

16. A method of cutting a drape for use with a negative pressure wound therapy device, the method comprising the steps of:
 placing a cutting template on a dressing;
 placing a drape over the cutting template such that the drape covers the cutting template and the dressing;
 pressing an implement against the drape such that the implement presses the drape towards the cutting template, thereby causing the drape to be cut;
 rotating, after pressing the implement against the drape such that the implement presses the drape towards the cutting template, the implement about the cutting template thereby causing a cutout to be separated from the drape and an aperture to be simultaneously formed in the drape;
 removing the cutout from the aperture;
 sealing a negative pressure lumen of the negative pressure wound therapy device about the aperture;
 rotating, prior to placing the cutting template on the dressing, the cutting template along a perimeter of a wound bed; and
 placing, prior to placing the cutting template on the dressing and after rotating the cutting template along the perimeter of the wound bed, the dressing over at least a portion of the wound bed.

17. The method of claim 16, further comprising the step of locating the cutting template on the dressing such that a dimple on the cutting template is received in a divot on the dressing.

* * * * *